US012805695B2

(12) United States Patent
Sato

(10) Patent No.: US 12,805,695 B2
(45) Date of Patent: Nov. 24, 2026

(54) METHOD, PROGRAM, AND APPARATUS FOR PREDICTING THE DETERIORATION AMOUNT OF A SUSPECTED LESION

(71) Applicant: PENTAX MEDICAL CORPORATION, Tokyo (JP)

(72) Inventor: Rei Sato, Tokyo (JP)

(73) Assignee: PENTAX MEDICAL CORPORATION, Tokyo (JP)

( * ) Notice: Subject to any disclaimer, the term of this patent is extended or adjusted under 35 U.S.C. 154(b) by 1210 days.

(21) Appl. No.: 17/298,275

(22) PCT Filed: Jul. 23, 2019

(86) PCT No.: PCT/JP2019/028894
§ 371 (c)(1),
(2) Date: May 28, 2021

(87) PCT Pub. No.: WO2021/014584
PCT Pub. Date: Jan. 28, 2021

(65) Prior Publication Data

US 2022/0095889 A1 Mar. 31, 2022

(51) Int. Cl.
*A61B 1/00* (2006.01)
*A61B 1/045* (2006.01)
*G06T 7/00* (2017.01)

(52) U.S. Cl.
CPC .......... *A61B 1/00009* (2013.01); *A61B 1/045* (2013.01); *G06T 7/0012* (2013.01); *G06T 2207/10068* (2013.01); *G06T 2207/20081* (2013.01); *G06T 2207/20084* (2013.01); *G06T 2207/30096* (2013.01)

(58) Field of Classification Search
None
See application file for complete search history.

(56) References Cited

U.S. PATENT DOCUMENTS

| | | | |
|---|---|---|---|
| 7,031,503 | B2 | 4/2006 | Ozaki et al. |
| 2004/0230458 | A1 | 11/2004 | Takayama et al. |
| 2007/0161853 | A1 | 7/2007 | Yagi et al. |
| 2011/0075900 | A1 | 3/2011 | Masumoto |
| 2015/0066818 | A1 | 3/2015 | Choi et al. |
| 2016/0092767 | A1 | 3/2016 | Osogami et al. |
| 2016/0270753 | A1 | 9/2016 | Kawamur |
| 2018/0279983 | A1 | 10/2018 | Ohishi |
| 2019/0034800 | A1 | 1/2019 | Shiratani |
| 2019/0272641 | A1 | 9/2019 | Akama et al. |
| 2019/0374088 | A1 | 12/2019 | Watanabe |

FOREIGN PATENT DOCUMENTS

| | | | |
|---|---|---|---|
| JP | 2001-204738 | 7/2001 | |
| JP | 2002-230517 | 8/2002 | |
| JP | 2004-280807 | 10/2004 | |
| JP | 2007-020872 | 2/2007 | |
| JP | 2011-92685 | 5/2011 | |
| JP | 2016-71697 | 5/2016 | |
| JP | 2016-529037 | 9/2016 | |
| JP | 2016-174735 | 10/2016 | |
| JP | 2018-22216 | 2/2018 | |
| JP | 2018-164738 | 10/2018 | |
| WO | 2005/077253 | 8/2005 | |
| WO | 2017/175282 | 10/2017 | |
| WO | WO-2017175282 A1 * | 10/2017 | ............. G06V 10/82 |
| WO | 2018/159363 | 9/2018 | |

OTHER PUBLICATIONS

Spencer et al. (Pediatric Anesthesia, 2015, vol. 25, pp. 301-308) (Year: 2015).*
Tajbakhsh et al. (IEEE Transactions on Medical Imaging, vol. 35, No. 5, May 2016, pp. 1299-1312) (Year: 2016).*
Jiang et al. (Computerized Medical Imaging and Graphics 34, 2010, 617-631) (Year: 2010).*
Official Communication issued in International Bureau of WIPO Patent Application No. PCT/JP2019/028894, dated Oct. 15, 2019 , along with an English translation thereof.
Office Action issued in Japan Counterpart Patent Appl. No. 2019-569984, dated Jan. 28, 2021.

* cited by examiner

*Primary Examiner* — Pablo S Whaley
(74) *Attorney, Agent, or Firm* — GREENBLUM & BERNSTEIN, P.L.C.

(57) ABSTRACT

A program causes a computer to execute processing of: acquiring a plurality of images captured by an endoscope over a predetermined period; and estimating a future state of an intracorporeal part included in the plurality of images on the basis of the plurality of acquired images.

4 Claims, 21 Drawing Sheets

FIG. 4

631

EXAMINATION RESULT DB

Relation

SUBJECT MASTER TABLE

| SUBJECT ID | SEX | DATE OF BIRTH | AGE | BMI | NATIONALITY |
|---|---|---|---|---|---|
| YA-002 | ... | ... | ... | ... | ... |
| HI-669 | ... | ... | ... | ... | ... |
| TU-123 | ... | ... | ... | ... | ... |

IMAGE MASTER TABLE

| SUBJECT ID | DATE OF EXAMINATION | ENDOSCOPE IMAGE (ON WHICH DISTANCE INFORMATION IS SUPERIMPOSED) | THREE-DIMENSIONAL MAP DATA | AMOUNT OF DETERIORATION FROM PREVIOUS EXAMINATION |
|---|---|---|---|---|
| YA-002 | 2019.05-01 | ya/190501.mp4 | 1234.xyz | rraa1.dat |
| YA-002 | 2018.05-01 | ya/180501.mp4 | 1235.xyz | rraa2.dat |
| YA-002 | 2017.05-01 | ya/170501.mp4 | 1236.xyz | rraa3.dat |
| YA-002 | 2016.05-01 | ya/160501.mp4 | 1237.xyz | rraa4.dat |
| HI-669 | 2019.04-01 | hi/190401.mp4 | 1238.xyz | rraa5.dat |
| HI-669 | 2018.04-01 | hi/180401.mp4 | 1239.xyz | rraa6.dat |
| TU-123 | 2019.03-01 | tu/190301.mp4 | 1240.xyz | rraa7.dat |

| PROBLEM DATA | | | | | ANSWER DATA | | |
|---|---|---|---|---|---|---|---|
| t−4 | t−3 | t−2 | t−1 | t | t+1 | t+2 | t+3 |
| 3 | 4 | 5 | 3 | 1 | 2 | 3 | 1 |
| 11 | 22 | 33 | 13 | 14 | 10 | 12 | 14 |
| ⋮ | ⋮ | ⋮ | ⋮ | ⋮ | ⋮ | ⋮ | ⋮ |
| ⋮ | ⋮ | ⋮ | ⋮ | ⋮ | ⋮ | ⋮ | ⋮ |
| ⋮ | ⋮ | ⋮ | ⋮ | ⋮ | ⋮ | ⋮ | ⋮ |
| ⋮ | ⋮ | ⋮ | ⋮ | ⋮ | ⋮ | ⋮ | ⋮ |

METHOD, PROGRAM, AND APPARATUS FOR PREDICTING THE DETERIORATION AMOUNT OF A SUSPECTED LESION

CROSS-REFERENCES TO RELATED APPLICATIONS

This application is a national stage application, under Section 371 of PCT application PCT/JP2019/028894, filed Jul. 23, 2019

BACKGROUND OF THE INVENTION

Field of the Invention

The present technology relates to a program, an information processing method, and an information processing apparatus.

Description of the Related Art Including Information Disclosed Under 37 CFR 1.97 and 37 CFR 1.98

Computer-aided diagnostic technology has been developed which automatically detects lesions using a learning model from medical images such as endoscope images. A method of generating a learning model by supervised machine learning using training data with a correct answer label is known.

A learning model is disclosed which learns by a learning method of combining a first learning using an image group captured by a normal endoscope as the training data and a second learning using an image group captured by a capsule endoscope as the training data (for example, see Patent Literature 1 cited in paragraph [0004]).

Patent Literature 1 cited in paragraph [0003] is WO 2017/175282A.

BRIEF SUMMARY OF THE INVENTION

However, the learning model described in Patent Literature 1 outputs information regarding a lesion such as a polyp or a tumor for diagnosis support on the basis of an input image. However, since the learning model outputs information regarding the lesion at the current time point when the image is captured, there is a problem that diagnosis support regarding how the state of a target affected part changes in the future is not considered.

In one aspect, an object is to provide a program or the like that provides diagnosis support regarding a future change in a target region of a subject.

A program according to an aspect of the present disclosure causes a computer to execute processing of: acquiring a plurality of images captured by an endoscope over a predetermined period; and estimating a future state of an intracorporeal part included in the plurality of images on the basis of the plurality of acquired images.

An information processing method according to an aspect of the present disclosure causes a computer to execute processing of: acquiring a plurality of images captured by an endoscope over a predetermined period; and estimating a future state of an intracorporeal part included in the plurality of images on the basis of the plurality of acquired images.

An information processing apparatus according to an aspect of the present disclosure includes: an acquisition unit that acquires a plurality of images captured by an endoscope over a predetermined period; and an estimation unit that estimates a future state of an intracorporeal part included in the plurality of images on the basis of the plurality of acquired images.

According to the present disclosure, it is possible to provide a program or the like that provides diagnosis support regarding a future change in a target region of a subject.

BRIEF DESCRIPTION OF THE SEVERAL VIEWS OF THE DRAWINGS

FIG. 4 is an explanatory diagram illustrating a data layout of an examination result DB.

FIG. 10 is a functional block diagram illustrating functional parts included in the control unit of the information processing apparatus or the like.

FIG. 17 is a functional block diagram illustrating functional parts included in the control unit of the information processing apparatus or the like.

FIG. 21 is a functional block diagram illustrating functional parts included in the control unit of the information processing apparatus or the like.

DETAILED DESCRIPTION OF THE INVENTION

First Embodiment

Figure 1:
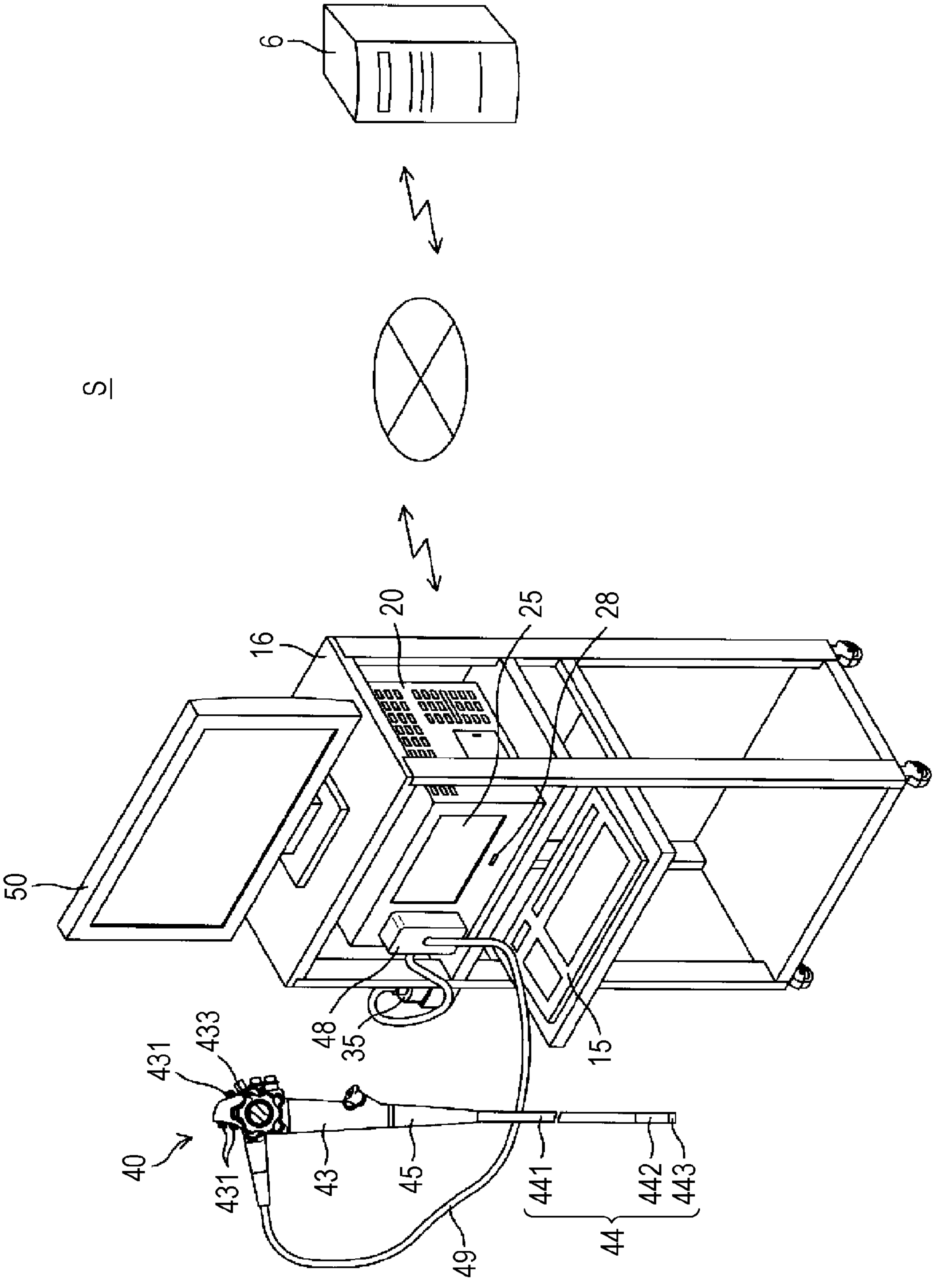
FIG. 1 is a schematic diagram illustrating an outline of a diagnosis support system according to a first embodiment.

Hereinafter, the present invention will be specifically described with reference to the drawings illustrating embodiments of the present invention. FIG. 1 is a schematic diagram illustrating an outline of a diagnosis support system S according to a first embodiment.

The diagnosis support system S includes an endoscope device 10 and an information processing apparatus 6 communicably connected to the endoscope device 10.

The endoscope device 10 transmits an image (captured image) captured by an image capturing element of an endoscope to a processor 20 for an endoscope, and the processor 20 for an endoscope performs various types of image processing such as gamma correction, white balance correction, and shading correction, thereby generating an endoscope image that is set to be easily viewed by an operator. The endoscope device 10 may further generate three-dimensional map data (three-dimensional texture mapped data reflecting the inner diameter of the body cavity) on the basis of the generated endoscope image. The endoscope device 10 outputs (transmits) the generated endoscope image and three-dimensional map data to the information processing apparatus 6. The information processing apparatus 6 that has acquired the endoscope image and three-dimensional map data transmitted from the endoscope device 10 performs various types of information processing on the basis of the endoscope image or three-dimensional map data, and outputs information regarding diagnosis support.

Figure 2:
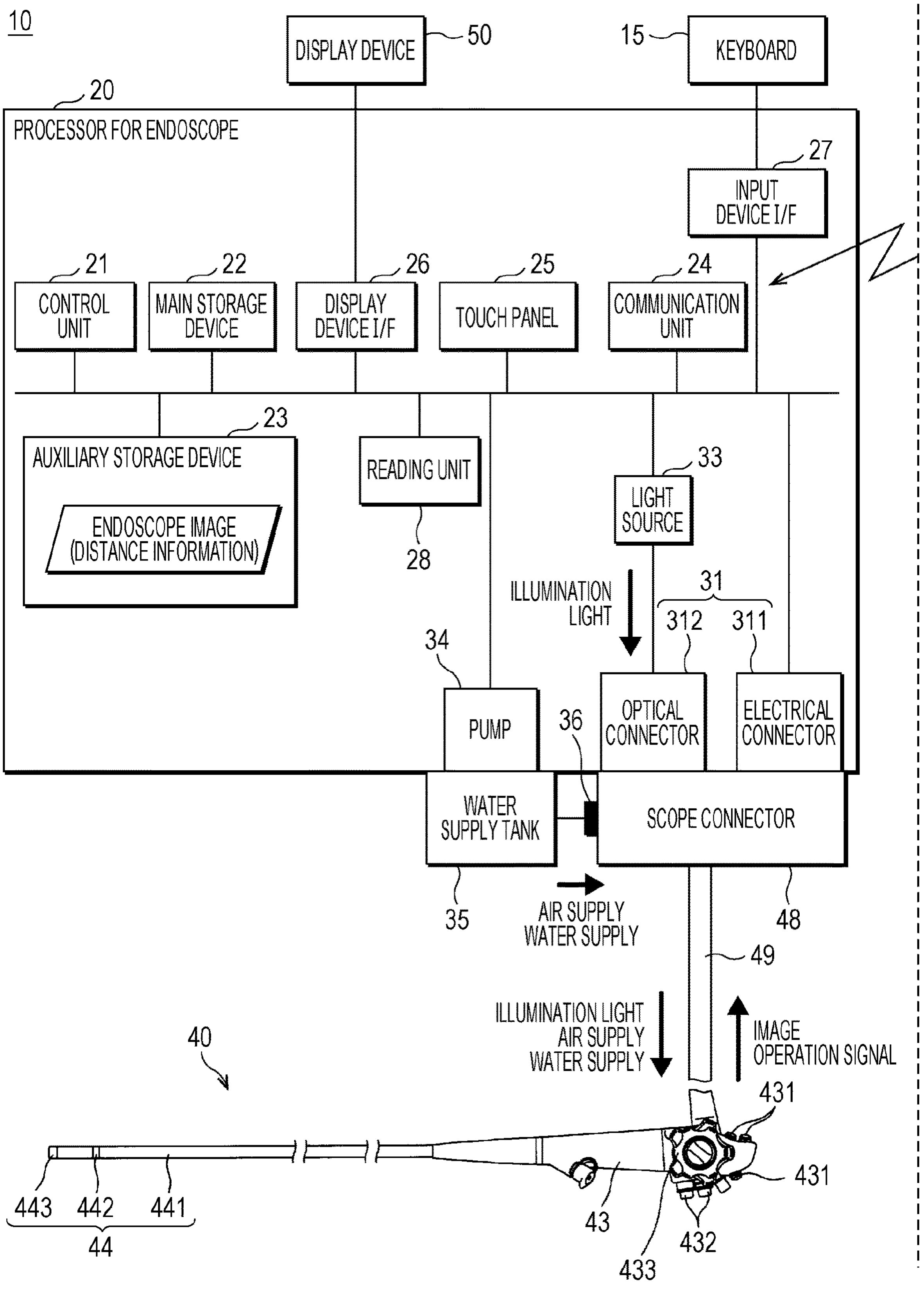
FIG. 2 is a block diagram illustrating a configuration example of an endoscope device included in the diagnosis support system.
Figure 3:
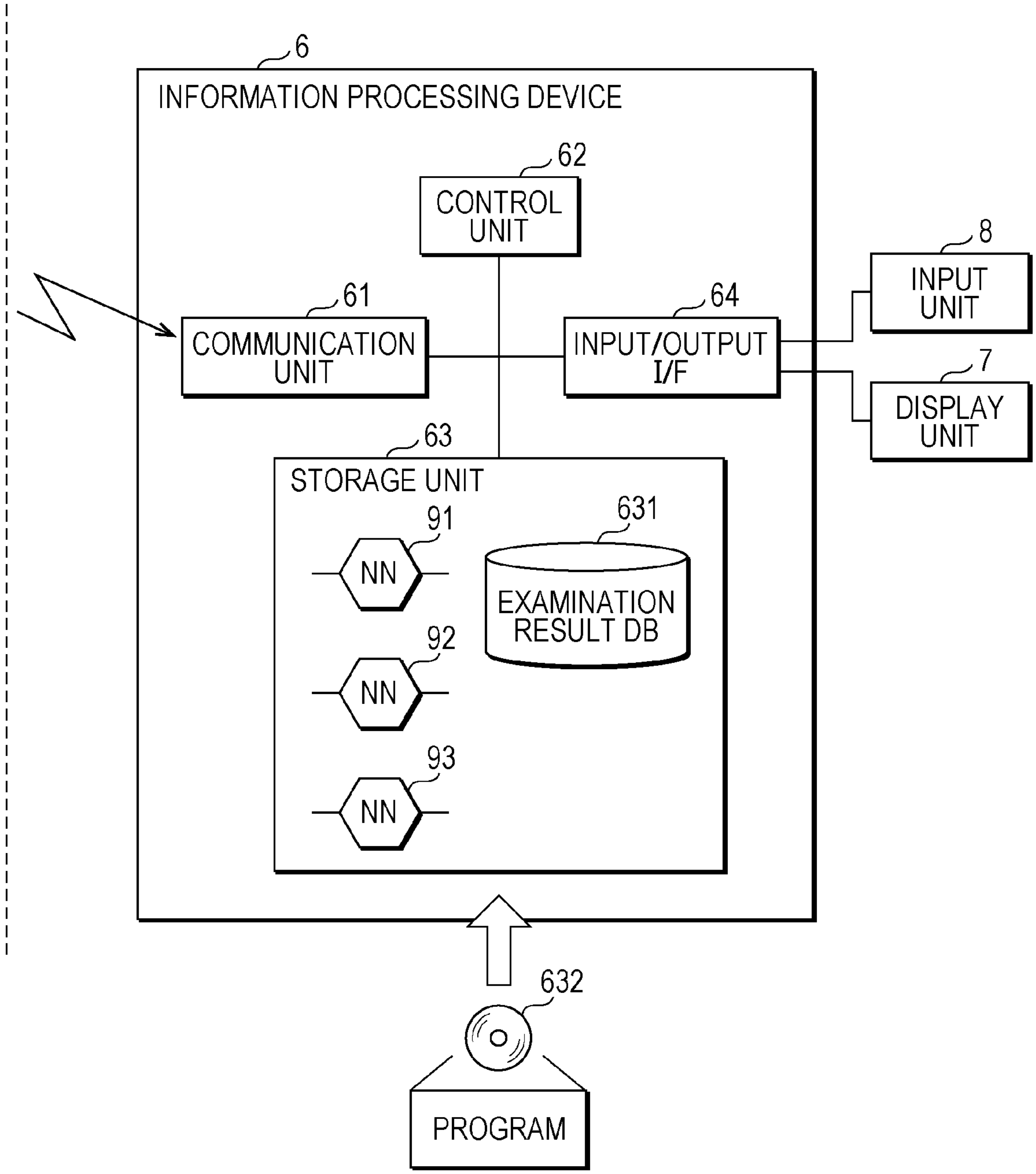
FIG. 3 is a block diagram illustrating a configuration example of an information processing apparatus included in the diagnosis support system.

FIG. 2 is a block diagram illustrating a configuration example of the endoscope device 10 included in the diagnosis support system S. FIG. 3 is a block diagram illustrating a configuration example of the information processing apparatus 6 included in the diagnosis support system S. The endoscope device 10 includes the processor 20 for an endoscope, an endoscope 40, and a display device 50. The display device 50 is, for example, a liquid crystal display device or an organic electro luminescence (EL) display device.

The display device 50 is installed on the upper stage of a storage shelf 16 with casters. The processor 20 for an endoscope is housed in the middle stage of the storage shelf 16. The storage shelf 16 is arranged in the vicinity of an endoscopic examination bed (not illustrated). The storage shelf 16 includes a pull-out shelf on which a keyboard 15 connected to the processor 20 for an endoscope is mounted.

The processor 20 for an endoscope has a substantially rectangular parallelepiped shape and includes a touch panel 25 provided on one surface thereof. A reading unit 28 is arranged below the touch panel 25. The reading unit 28 is a connection interface for performing reading and writing on a portable recording medium such as a USB connector, a secure digital (SD) card slot, or a compact disc read only memory (CD-ROM) drive.

The endoscope 40 includes an insertion portion 44, an operation unit 43, a flexible light guide tube 49, and a scope connector 48. The operation unit 43 is provided with a control button 431. The insertion portion 44 is long, and has one end connected to the operation unit 43 via a bend preventing portion 45. The insertion portion 44 has a soft portion 441, a bending portion 442, and a distal tip 443 in the order from the operation unit 43. The bending portion 442 is bent according to an operation of a bending knob 433. Physical detection devices such as a three-axis acceleration sensor, a gyro sensor, a geomagnetic sensor, and a magnetic coil sensor may be mounted on the insertion portion 44, and when the endoscope 40 is inserted into the body of the subject, detection results from these physical detection devices may be acquired.

The flexible light guide tube 49 is long, and has a first end connected to the operation unit 43 and a second end connected to the scope connector 48. The flexible light guide tube 49 is flexible. The scope connector 48 has a substantially rectangular parallelepiped shape. The scope connector 48 is provided with an air/water supply port 36 (see FIG. 2) for connecting an air/water supply tube.

The endoscope device 10 includes the processor 20 for an endoscope, an endoscope 40, and a display device 50. In addition to the touch panel 25 and the reading unit 28, the processor 20 for an endoscope includes a control unit 21, a main storage device 22, an auxiliary storage device 23, a communication unit 24, a display device interface (I/F) 26, an input device I/F 27, an endoscope connector 31, a light source 33, a pump 34, and a bus. The endoscope connector 31 includes an electric connector 311 and an optical connector 312.

The control unit 21 is an arithmetic control device that executes a program of the present embodiment. One or more central processing units (CPUs), graphics processing units (GPUs), or multi-core CPUs, and the like are used for the control unit 21. The control unit 21 is connected to each hardware unit constituting the processor 20 for an endoscope via the bus.

The main storage device 22 is, for example, a storage device such as a static random access memory (SRAM), a dynamic random access memory (DRAM), or a flash memory. The main storage device 22 temporarily stores information necessary during the processing performed by the control unit 21 and a program being executed by the control unit 21. The auxiliary storage device 23 is, for example, a storage device such as an SRAM, a flash memory, or a hard disk, and is a storage device having a larger capacity than the main storage device 22. In the auxiliary storage device 23, for example, the acquired captured image, and the generated endoscope image or three-dimensional map data may be stored as intermediate data.

The communication unit 24 is a communication module or a communication interface for performing communication with the information processing apparatus via a network in a wired or wireless manner, and is, for example, a narrow-area wireless communication module such as Wi-Fi (registered trademark) or Bluetooth (registered trademark) or a wide-area wireless communication module such as 4G or LTE. The touch panel 25 includes a display unit such as a liquid crystal display panel, and an input unit layered on the display unit.

The display device I/F 26 is an interface for connecting the processor 20 for an endoscope and the display device 50 to each other. The input device OF 27 is an interface for connecting the processor 20 for an endoscope and an input device such as the keyboard 15 to each other.

The light source 33 is a high-intensity white light source such as a xenon lamp. The light source 33 is connected to the bus via a driver (not illustrated). The on/off and brightness change of the light source 33 are controlled by the control unit 21. Illumination light emitted from the light source 33 is incident on the optical connector 312. The optical connector 312 engages with the scope connector 48 to supply the illumination light to the endoscope 40.

The pump 34 generates a pressure for the air supply/water supply function of the endoscope 40. The pump 34 is connected to the bus via a driver (not illustrated). The on/off and pressure change of the pump 34 are controlled by the control unit 21. The pump 34 is connected to the air/water supply port 36 provided in the scope connector 48 via a water supply tank 35.

The function of the endoscope 40 connected to the processor 20 for an endoscope will be outlined. A fiber bundle, a cable bundle, an air supply tube, a water supply tube, and the like are inserted inside the scope connector 48, the flexible light guide tube 49, the operation unit 43, and the insertion portion 44. The illumination light emitted from the light source 33 is radiated from an illumination window provided at the distal tip 443 via the optical connector 312 and the fiber bundle. The range illuminated by the illumination light is captured by an image sensor provided at the distal tip 443. The captured image is transmitted from the image sensor to the processor 20 for an endoscope via the cable bundle and the electric connector 311.

The control unit 21 of the processor 20 for an endoscope executes a program stored in the main storage device 22 to function as an image processing unit and a distance deriving unit. The image processing unit performs various types of image processing such as gamma correction, white balance correction, and shading correction on an image (captured image) output from the endoscope, and outputs the image as the endoscope image.

The distance deriving unit derives information on a distance from the image sensor (the image sensor provided at the distal tip 443) to an intracorporeal part (organ inner wall) on the basis of the endoscope image or the captured image. The distance information can be derived using, for example, monocular distance image estimation, a time of flight (TOF) method, a pattern irradiation method, or the like. Alternatively, a processing routine based on a three-dimensional simultaneous localization and mapping (SLAM) technology may be executed to create an environmental map in which the organ inner wall of the body cavity is set as a surrounding environment and estimate the position of the image sensor on the basis of the image of the intracorporeal part in the body cavity captured by the image sensor, thereby deriving the distance between the image sensor and the target intracorporeal part. In deriving the distance information, for example, the distance information deriving unit may process data obtained by the physical detection system device such as a three-axis acceleration sensor, a gyro sensor, a geomagnetic sensor, a magnetic coil sensor, or a mouthpiece with an insertion amount detection function in association with a captured image, the physical detection system device being mounted on the insertion portion 44 of the endoscope 40, or may use the data in combination with a radiation image.

The image processing unit further acquires the distance information derived by the distance information deriving unit, performs three-dimensional texture mapping reflecting the inner diameter of the body cavity on the basis of the distance information and an image subjected to transformation processing, and generates the three-dimensional map data. The generated three-dimensional map data includes three-dimensional coordinates of an intracorporeal part included in the captured image. In generating the three-dimensional map data, the image processing unit may apply an image texture by using transformation processing such as affine transformation and projective transformation.

The information processing apparatus 6 includes a control unit 62, a communication unit 61, a storage unit 63, and an input/output I/F 64. The control unit 62 includes one or more arithmetic processing devices having a time counting function, such as a central processing unit (CPU), a micro-processing unit (MPU), and a graphics processing unit (GPU), and reads and executes a program P stored in the storage unit 63, thereby performing various types of information processing, control processing, and the like related to the information processing apparatus 6. Alternatively, the control unit 62 may include a quantum computer chip, and the information processing apparatus 6 may be a quantum computer.

The storage unit 63 includes a volatile storage region such as a static random access memory (SRAM), a dynamic random access memory (DRAM), or a flash memory, and a nonvolatile storage region such as an EEPROM or a hard disk. The storage unit 63 stores in advance the program P and data to be referred to at the time of processing. The program P stored in the storage unit 63 may be a program P read from a recording medium 632 readable by the information processing apparatus 6. Alternatively, the program P may be downloaded from an external computer (not illustrated) connected to a communication network (not illustrated) and be stored in the storage unit 63. The storage unit 63 stores an entity file (instance file of a neural network (NN)) constituting a peristalsis-amount-learned model 91, a deterioration-amount-learned model 92, and a corrected-deterioration-amount-learned model 93 to be described later. These entity files may be configured as a part of the program P. The storage unit 63 stores an examination result database (DB) 631 to be described later.

The communication unit 61 is a communication module or a communication interface for performing communication with the endoscope device 10 in a wired or wireless manner, and is, for example, a narrow-area wireless communication module such as Wi-Fi (registered trademark) or Bluetooth (registered trademark) or a wide-area wireless communication module such as 4G or LTE.

The input/output I/F 64 is compliant with a communication standard such as USB or DSUB, for example, and is a communication interface for performing serial communication with an external device connected to the input/output I/F 64. For example, a display unit 7 such as a display and an input unit 8 such as a keyboard are connected to the input/output I/F 64, and the control unit 62 outputs, to the display unit 7, a result of information processing performed on the basis of an execution command or an event, input from the input unit 8.

FIG. 4 is an explanatory diagram illustrating a data layout of the examination result DB 631. The examination result DB 631 is stored in the storage unit 63 of the information processing apparatus 6, and includes database management software such as a relational database management system (RDBMS) implemented in the information processing apparatus 6.

The examination result DB 631 includes, for example, a subject master table and an image table, and the subject master table and the image table are associated with each other by a subject ID that is an item (metadata) included in both tables.

The subject master table includes, for example, a subject ID, sex, date of birth, age, a body mass index (BMI), and nationality as management items (metadata). In the item (field) of the subject ID, ID information is stored in order to uniquely identify the subject who has undergone the endoscopic examination. The biological attributes of the sex and the date of birth of the subject ID are stored in the items (fields) of the sex and the date of birth, and the age at the current time point calculated by the date of birth is stored in the item (field) of the age. Similarly, information regarding the value of the BMI and the nationality of the subject ID is stored in the BMI and the nationality. The sex, the age, the BMI, and the nationality are managed as biological information of the subject by the subject master table.

The image table includes, as management items (metadata), for example, a subject ID, a date of examination, an endoscope image, three-dimensional map data, and the amount of deterioration from a previous examination. The item (field) of the subject ID is for association with the biological attributes of the subject managed in the subject master table, and stores the value of the ID of each subject. The item (field) of the date of examination stores the date when the subject corresponding to the subject ID has undergone the endoscopic examination. In the item (field) of the endoscope image, the endoscope image of the subject ID is stored as object data. Alternatively, the item (field) of the endoscope image may store information indicating a storage location (file path) of the endoscope image stored as a file. In the item (field) of the three-dimensional map data, three-dimensional map data of the subject ID is stored as object data. Alternatively, information indicating a storage location (file path) of the three-dimensional map data stored as a file may be stored in the item (field) of the three-dimensional map data. The item (field) of the amount of deterioration from the previous examination stores information regarding the deterioration amount of a predetermined intracorporeal part based on the comparison between a current examination and the previous examination. In the storage of the deterioration amount, the value of the deterioration amount of each of a plurality of intracorporeal parts may be stored, for example, in an array. Alternatively, each deterioration amount for each pixel may be stored and saved in an array in a unit of pixel in the endoscope image.

Figure 5:
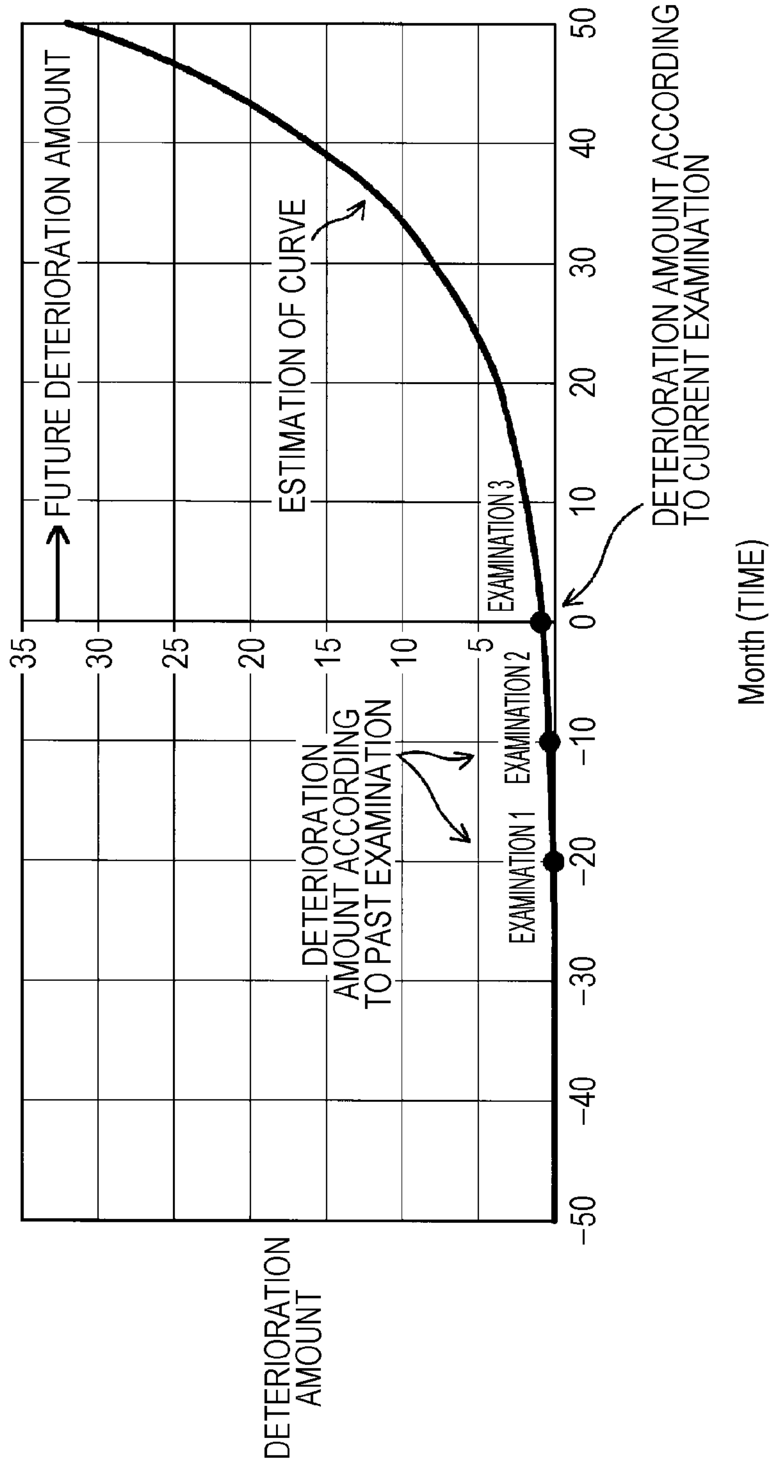
FIG. 5 is an explanatory diagram regarding a graph showing a deterioration estimation line.

FIG. 5 is an explanatory diagram regarding a graph showing a deterioration estimation line. The information processing apparatus 6 estimates the future state of the intracorporeal part included in the plurality of images on the basis of the plurality of acquired images (time-series images) captured over a predetermined period, and the graph showing the deterioration estimation line illustrated in FIG. 5 is obtained by graphically displaying the estimation result. The horizontal axis of the graph showing the deterioration estimation line represents time, and the vertical axis indicates values of the current and past deterioration amounts and the future deterioration amount (deterioration prediction value). As illustrated in the drawing, three deterioration amounts are plotted on the basis of the past and current examinations. On the basis of the past and current deterioration amounts, an approximate line indicating the future deterioration amount (deterioration prediction value) is displayed as the deterioration prediction line.

The information processing apparatus 6 acquires the endoscope image and distance information (or the endoscope image on which the distance information is superimposed) output from the processor 20 for an endoscope or an image such as the three-dimensional map data (an image obtained by the current examination), and acquires an image in the past examination (an image obtained by the past examination) corresponding to the image by referring to the examination result DB 631. The current and past images are images related to results of the same subject, and the information processing apparatus 6 acquires a plurality of images (time-series images) captured over a predetermined period on the basis of the current and past images. The number of images obtained by the past examination is preferably plural, but may be one.

The information processing apparatus 6 extracts a feature amount on the basis of the image obtained by the current examination. The feature amount specifies an intracorporeal part suspected of being a lesion at present or in the future, and may be used to derive the deterioration amount by using, for example, edge detection, pattern recognition, or a learned model such as a neural network to be described later.

The information processing apparatus 6 may store, as the information regarding the extracted feature amount, position information or shape information (including the size) of the intracorporeal part corresponding to the feature amount in the endoscope image on which the distance information is superimposed or the three-dimensional map data, in the storage unit 63. Alternatively, the information processing apparatus 6 may store, in the storage unit 63, a frame number of an image including an intracorporeal part corresponding to the feature amount and information (a pixel number, coordinates in an image coordinate system) regarding a region of the intracorporeal part in a frame (still image) of the image. Furthermore, the information processing apparatus 6 may store, as the information regarding the extracted feature amount, information regarding the color of the intracorporeal part corresponding to the feature amount (the value of each pixel element) in the storage unit 63.

The information processing apparatus 6 extracts a portion (the feature amount in the past image) corresponding to the feature amount (the feature amount in the current image) extracted from the image obtained by the current examination from each of the plurality of images obtained by the current examination. The information processing apparatus 6 extracts a difference (feature amount difference information) between the feature amounts adjacent in time series among the extracted current and past feature amounts.

The information processing apparatus 6 derives the deterioration amount of the intracorporeal part specified by the extracted feature amount on the basis of the extracted feature amount difference information. The information processing apparatus 6 may derive the deterioration amount on the basis of the change amounts of the color (the difference in the value of the pixel element), the position, or the shape (including the size) of the intracorporeal part specified by the feature amounts in the extracted feature amount difference information. Alternatively, the information processing apparatus 6 may derive the deterioration amount by using a learned model such as a neural network to be described later.

As illustrated in FIG. 5, an examination 3 is the deterioration amount in the current examination, and is derived on the basis of the difference information between the feature amounts of the current examination and the previous examination. An examination 2 is the deterioration amount in the previous examination, and is derived on the basis of the difference information between the feature amounts of the previous examination and an examination performed before the previous examination. An examination 1 is the deterioration amount in the examination performed before the previous examination, and is derived on the basis of the difference information between the feature amounts of the examination performed before the previous examination and an examination performed three times ago. On the basis of the plurality of derived deterioration amounts, the information processing apparatus 6 generates a graph showing the deterioration estimation line illustrated in FIG. 5 by using, for example, a linear approximation or a nonlinear approximation method, and outputs the graph to the display unit 7.

The information processing apparatus 6 can derive (estimate) a deterioration amount at an arbitrary time point in the future on the basis of the deterioration estimation line. The estimated deterioration amount is information related to the future health condition of the subject, and can be used as diagnosis support information for a doctor or the like.

Figure 6:
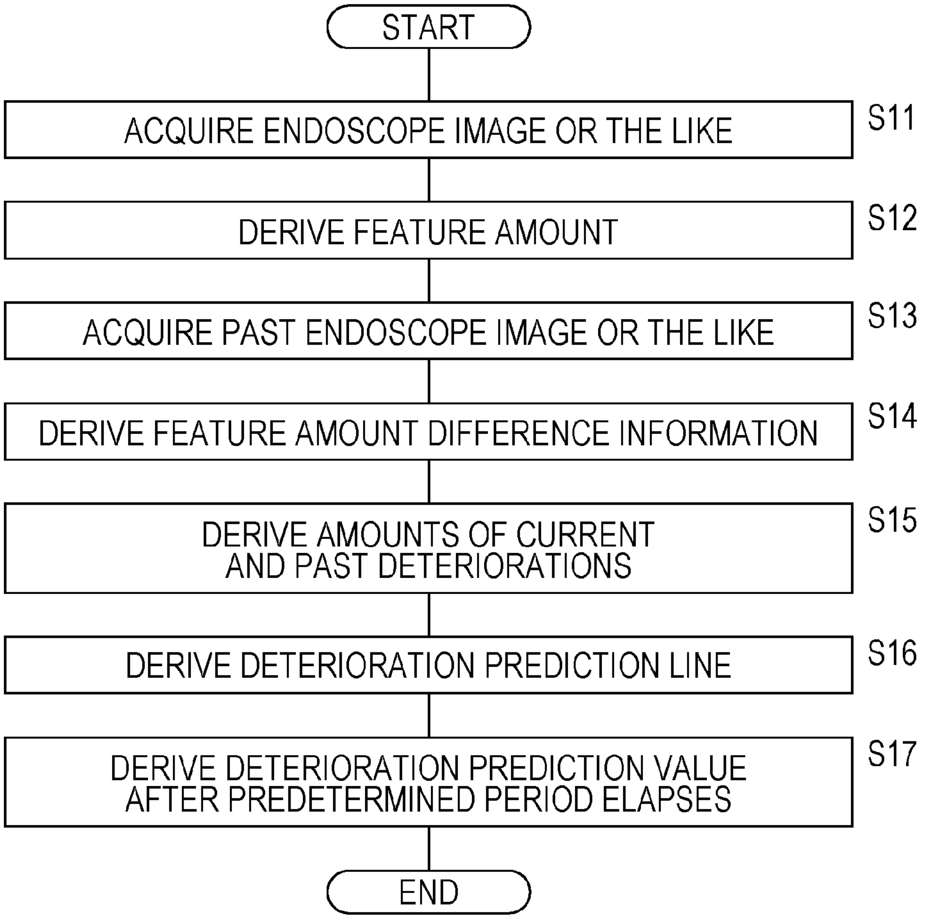
FIG. 6 is a flowchart illustrating an example of a processing procedure performed by a control unit of the information processing apparatus.

FIG. 6 is a flowchart illustrating an example of a processing procedure performed by the control unit 62 of the information processing apparatus 6. For example, the information processing apparatus 6 starts the processing of the flowchart on the basis of a content input through the input unit 8 connected to the information processing apparatus 6 itself.

The control unit 62 of the information processing apparatus 6 acquires the endoscope image or the like output from the processor 20 for an endoscope (S11). The control unit 62 acquires the captured image, the endoscope image (the endoscope image on which the distance information is superimposed), the three-dimensional map data, and the subject ID output from the processor 20 for an endoscope.

The control unit 62 of the information processing apparatus 6 derives the feature amount from the acquired endoscope image or the like (S12). The control unit 62 of the information processing apparatus 6 acquires the past endoscope image or the like by referring to the examination result DB 631 on the basis of the acquired subject ID (S13).

The control unit 62 of the information processing apparatus 6 derives the feature amount difference information (S14). The control unit 62 derives the feature amount difference information on the basis of the acquired feature amount in the current endoscope image and the feature amount in the past endoscope image corresponding to the feature amount (current feature amount).

The control unit 62 of the information processing apparatus 6 derives the current and past deterioration amounts on the basis of the difference information (S15). The control unit 62 derives the deterioration amount on the basis of the change amounts of the color, shape, and the like of the intracorporeal part, specified by the feature amounts included in the difference information.

The control unit 62 of the information processing apparatus 6 derives the deterioration prediction line on the basis of the current and past deterioration amounts (S16). The control unit 62 derives the deterioration prediction line by using, for example, a linear approximation or nonlinear approximation method on the basis of the current and past deterioration amounts, that is, a plurality of deterioration amounts arranged in time series.

The control unit 62 of the information processing apparatus 6 derives the deterioration prediction value after a predetermined period elapses (S17). The control unit 62 derives the deterioration prediction value at one or more time points after a predetermined period elapses from the current time point (a time point of the current examination) on the basis of the derived deterioration prediction line.

Second Embodiment

Figure 7:
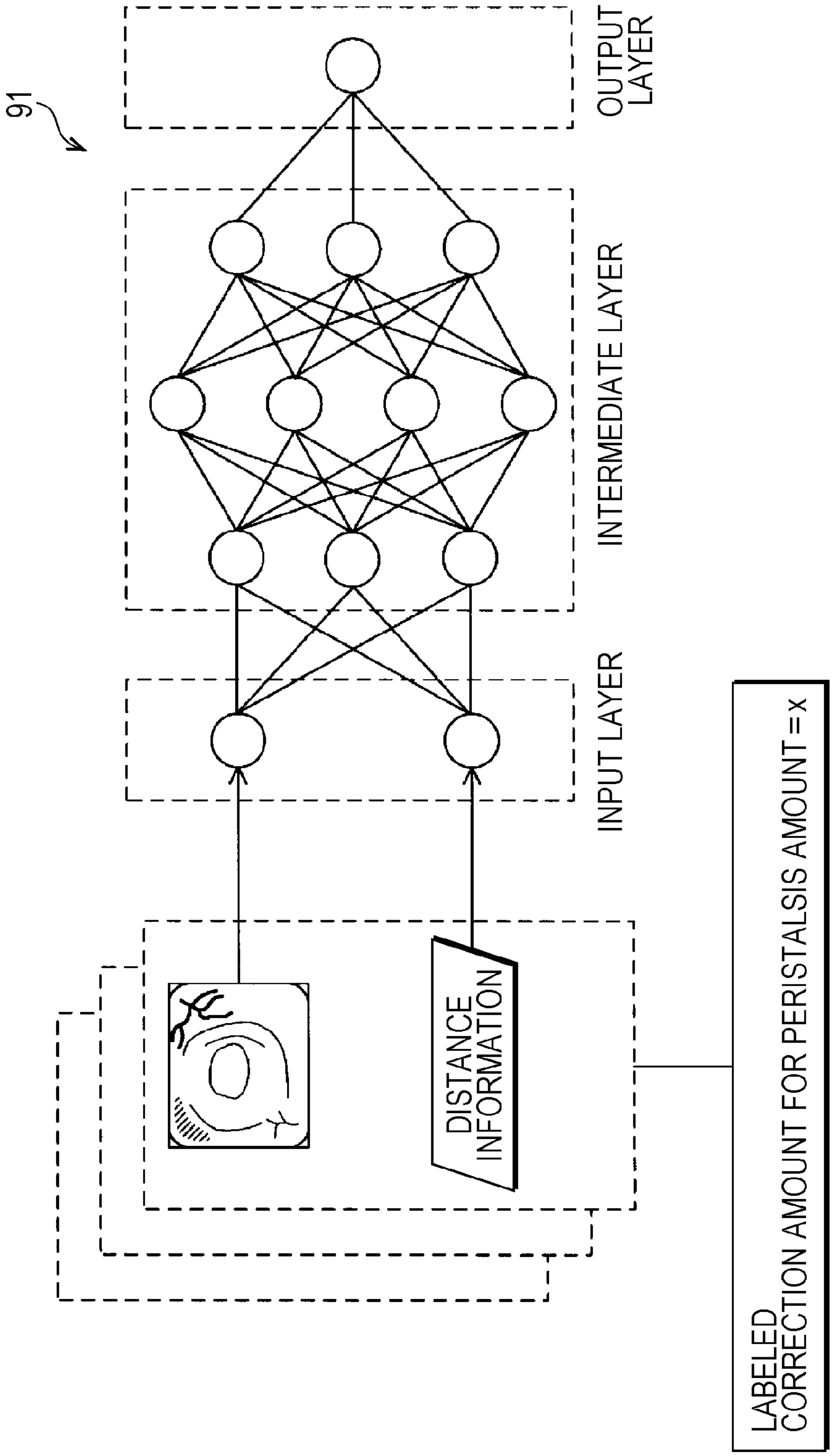
FIG. 7 is an explanatory diagram regarding processing of generating a peristalsis-amount-learned model according to a second embodiment.

FIG. 7 is an explanatory diagram regarding processing of generating the peristalsis-amount-learned model 91. An information processing apparatus 6 of a second embodiment is different from that of the first embodiment in that correction processing is performed by using a learned model such as the peristalsis-amount-learned model 91 in deriving the deterioration amount.

The information processing apparatus 6 constructs (generates) a neural network that receives the endoscope image and the distance information and outputs a correction amount for the peristalsis amount by performing learning on the basis of training data having the endoscope image and the distance information as problem data and having the correction amount for the peristalsis amount as answer data.

The neural network (peristalsis-amount-learned model 91) trained by using the training data is assumed to be used as a program P module that is a part of artificial intelligence software. The peristalsis-amount-learned model 91 is used in the information processing apparatus 6 including the control unit 62 (a CPU or the like) and the storage unit 63 as described above, and is executed by the information processing apparatus 6 having arithmetic processing capability, thereby configuring a neural network system. That is, the control unit 62 of the information processing apparatus 6 is operated to perform an arithmetic operation of extracting the feature amounts of the endoscope image and the distance information input to an input layer according to a command from the peristalsis-amount-learned model 91 stored in the storage unit 63, and output the correction amount for the peristalsis amount from an output layer.

The input layer has a plurality of neurons that receive the input of the pixel value of each pixel included in the endoscope image and the distance information, and transfers the input pixel value and distance information to an intermediate layer. The intermediate layer has a plurality of neurons that extract the image feature amount of the endoscope image, and transfers the extracted image feature amount and the active state of the neuron based on the input distance information to the output layer. For example, in a case where the peristalsis-amount-learned model is a CNN, the intermediate layer has a configuration in which a convolution layer that convolves the pixel value of each pixel input from the input layer and a pooling layer that maps (compresses) the pixel value convolved by the convolution layer are alternately connected, and the feature amount of the endoscope image is finally extracted while pixel information of the endoscope image is compressed. The output layer has one or more neurons that output information regarding the correction amount for the peristalsis amount in the intracorporeal part included in the endoscope image, and outputs information regarding the correction amount for the peristalsis amount on the basis of the image feature amount and the like output from the intermediate layer. The information regarding the output correction amount for the peristalsis amount is used as, for example, information for correcting the vertical arrangement of the organ surface (intracorporeal part) in the three-dimensional map data.

In the present embodiment, the data input to the peristalsis-amount-learned model 91 is described as the endoscope image, but the present invention is not limited thereto. The data input to the peristalsis-amount-learned model 91 may be a captured image captured by the image sensor. That is, the peristalsis-amount-learned model 91 may output information regarding the correction amount for the peristalsis amount, as the captured image and the distance information are input.

In the present embodiment, the peristalsis-amount-learned model 91 is described as a neural network (NN) such as a CNN, but the peristalsis-amount-learned model 91 is not limited to the NN, and may be a learned model constructed by another learning algorithm such as a support vector machine (SVM), a Bayesian network, or a regression tree.

The information processing apparatus 6 compares the value output from the output layer with information (the correction amount for the peristalsis amount) labeled for the training data (the endoscope image and the distance information), that is, a correct answer value (answer data), and optimizes a parameter used for the arithmetic processing in the intermediate layer so that the output value from the output layer approaches the correct answer value. The parameter is, for example, a weight (coupling coefficient) between neurons, a coefficient of an activation function used in each neuron, or the like. The parameter optimization method is not particularly limited, but for example, the information processing apparatus 6 optimizes various parameters using backpropagation. The information processing apparatus 6 performs the above-described processing on the endoscope image and the distance information included in the training data, generates the peristalsis-amount-learned model 91, and stores the generated peristalsis-amount-learned model 91 in the storage unit 63.

The endoscope image and the distance information (problem data) used as the training data and the information (answer data) regarding the peristalsis amount correlated with this information are stored in a large amount as the result data of the endoscopic examination performed in each medical institution, and it is possible to generate a large amount of training data for training the peristalsis-amount-learned model 91, by using these result data.

Figure 8:
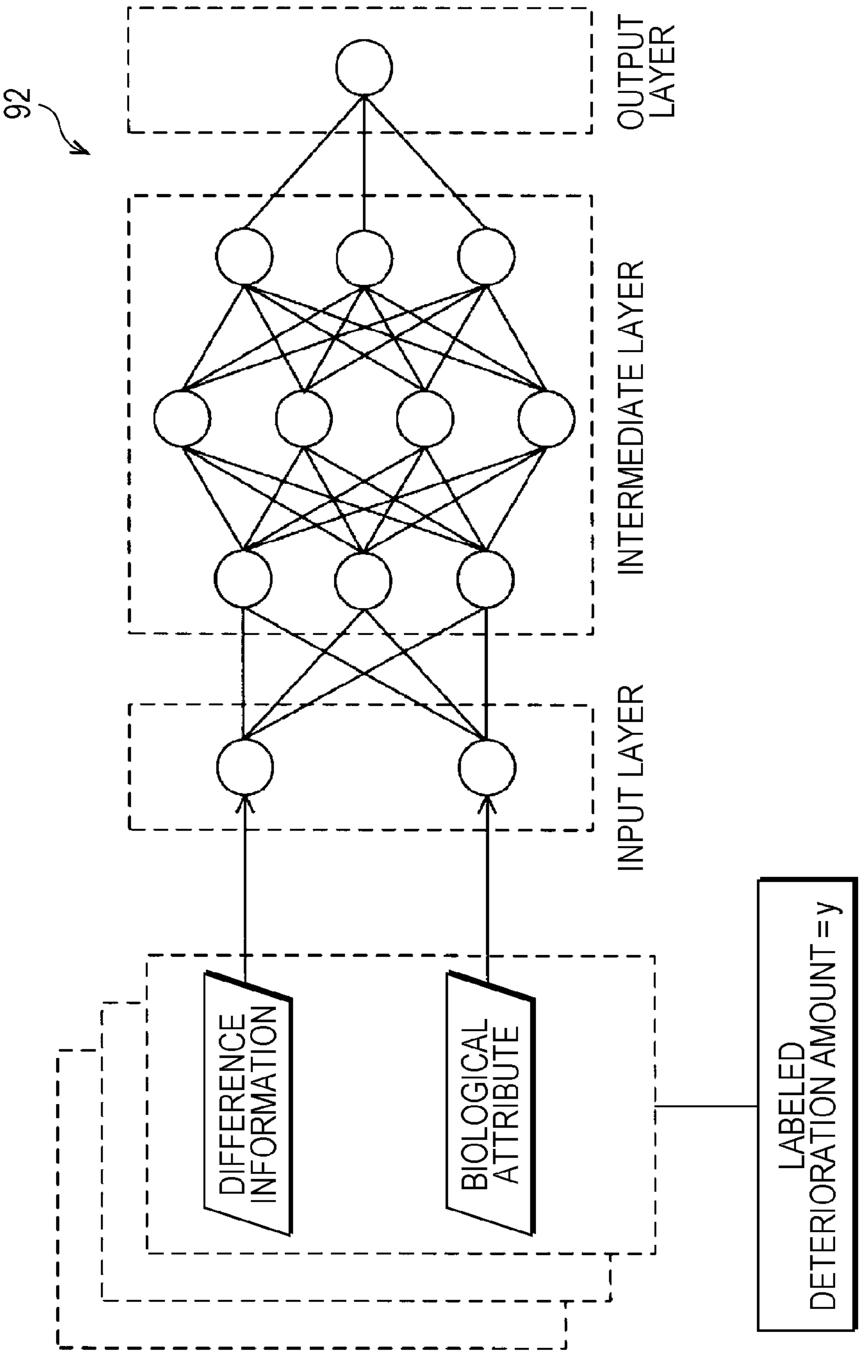
FIG. 8 is an explanatory diagram regarding processing of generating a deterioration-amount-learned model.

FIG. 8 is an explanatory diagram regarding processing of generating the deterioration-amount-learned model 92. The information processing apparatus 6 constructs (generates) a neural network that receives the difference information and the biological information and outputs the deterioration amount by performing learning on the basis of training data having the difference information and the biological information as the problem data and having the deterioration amount as the answer data. The difference information is information derived by a difference information deriving unit 624 (see FIG. 10) to be described later, and is derived on the basis of a difference between three-dimensional map data generated on the basis of the current endoscope image and three-dimensional map data generated on the basis of the past endoscope image. The biological information includes the age and the like of the subject, and is derived by referring to the examination result DB 631 on the basis of the subject ID that specifies the subject. The derivation of this information will be described later.

The input layer has a plurality of neurons that receive the input of the difference information and the biological information, and transfers the input difference information and biological information to the intermediate layer. The intermediate layer has, for example, a single phase or multilayer structure including one or more fully-connected layers, and each of the plurality of neurons included in the fully-connected layer outputs information indicating activation or deactivation on the basis of the value of the input difference information and biological information. The output layer has one or more neurons that output information regarding the deterioration amount of the intracorporeal part included in the endoscope image, and outputs the deterioration amount on the basis of the information indicating activation or deactivation of each neuron output from the intermediate layer.

Similarly to the peristalsis-amount-learned model 91, the information processing apparatus 6 optimizes the parameter used for the arithmetic processing in the intermediate layer of the deterioration-amount-learned model 92. The deterioration-amount-learned model 92 is assumed to be used as the program P module that is a part of the artificial intelligence software, similarly to the peristalsis-amount-learned model 91. In addition, the deterioration-amount-learned model 92 is not limited to the NN, similarly to the peristalsis-amount-learned model 91, and may be a learned model constructed by another learning algorithm such as an SVM. As for the difference information (problem data) used as the training data and the information (answer data) regarding the deterioration amount correlated with this information, the endoscope image and the distance information, which are original data for deriving these data, are stored in a large amount as the result data of the endoscopic examination performed in each medical institution. Therefore, by using these result data, it is possible to generate a large amount of training data for training the deterioration-amount-learned model 92.

Figure 9:
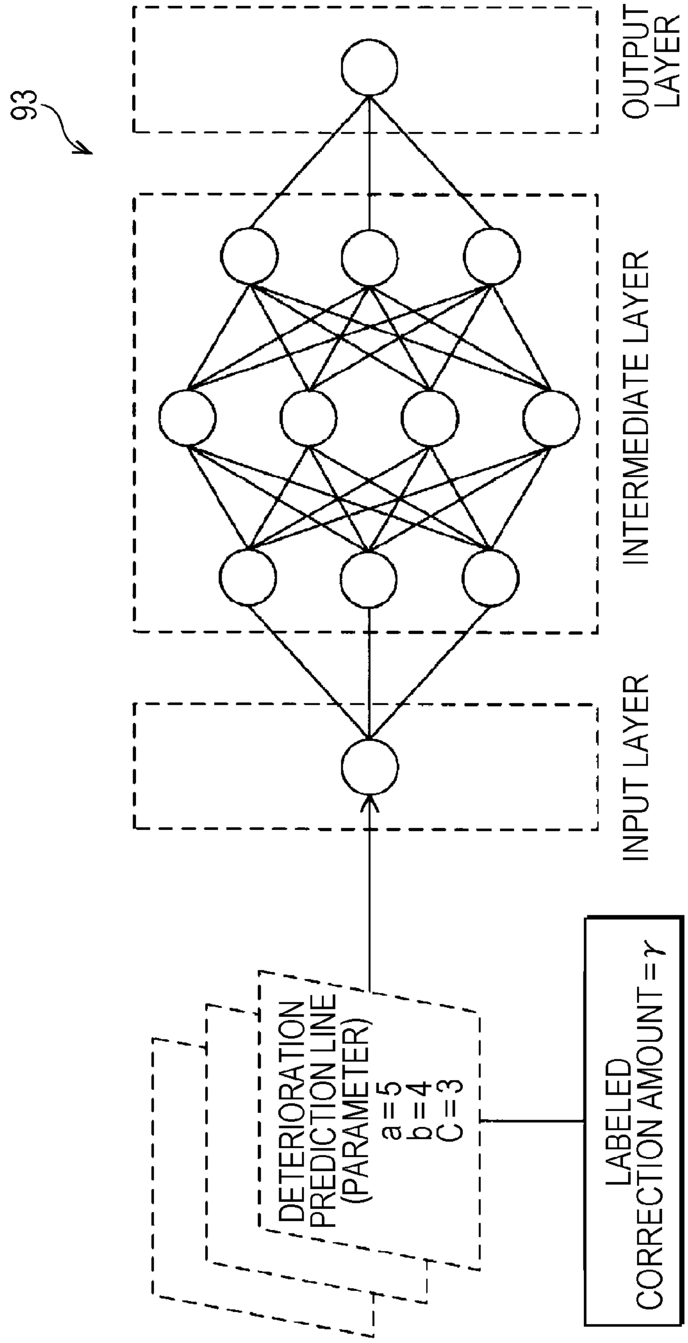
FIG. 9 is an explanatory diagram regarding processing of generating a corrected-deterioration-amount-learned model.

FIG. 9 is an explanatory diagram regarding processing of generating the corrected-deterioration-amount-learned model 93. The information processing apparatus 6 constructs (generates) a neural network that receives the deterioration prediction line and outputs the correction amount for the deterioration prediction line by performing learning on the basis of training data having the deterioration prediction line (the value of the parameter of the deterioration prediction line) as the problem data and having the correction amount for the deterioration prediction line as the answer data. The deterioration prediction line is information derived by a deterioration prediction line deriving unit 625 (see FIG. 10) to be described later, and is derived on the basis of the current and past deterioration amounts.

The input layer has a plurality of neurons that receive the input of the deterioration prediction line (the value of the parameter of the deterioration prediction line), and transfers each input value of the parameter of the deterioration prediction line to the intermediate layer. The intermediate layer has, for example, a single phase or multilayer structure including one or more fully-connected layers, and each of the plurality of neurons included in the fully-connected layer outputs information indicating activation or deactivation on the basis of each input value of the parameter of the deterioration prediction line. The output layer has one or more neurons that output information regarding the correction amount for the deterioration prediction line, and outputs the correction amount on the basis of information indicating activation or deactivation of each neuron output from the intermediate layer.

Similarly to the peristalsis-amount-learned model 91, the information processing apparatus 6 optimizes the parameter used for the arithmetic processing in the intermediate layer of the corrected-deterioration-amount-learned model 93. The corrected-deterioration-amount-learned model 93 is assumed to be used as the program P module that is a part of the artificial intelligence software, similarly to the peristalsis-amount-learned model 91. In addition, the corrected-deterioration-amount-learned model 93 is not limited to the NN, similarly to the peristalsis-amount-learned model 91, and may be a learned model constructed by another learning algorithm such as an SVM. As for the deterioration prediction line (the value of the parameter of the deterioration prediction line/problem data) used as the training data and the correction amount (answer data), the endoscope image and the distance information, which are original data for deriving these data, are stored in a large amount as the result data of the endoscopic examination performed in each medical institution. Therefore, by using these result data, it is possible to generate a large amount of training data for training the corrected-deterioration-amount-learned model 93.

Figure 10:
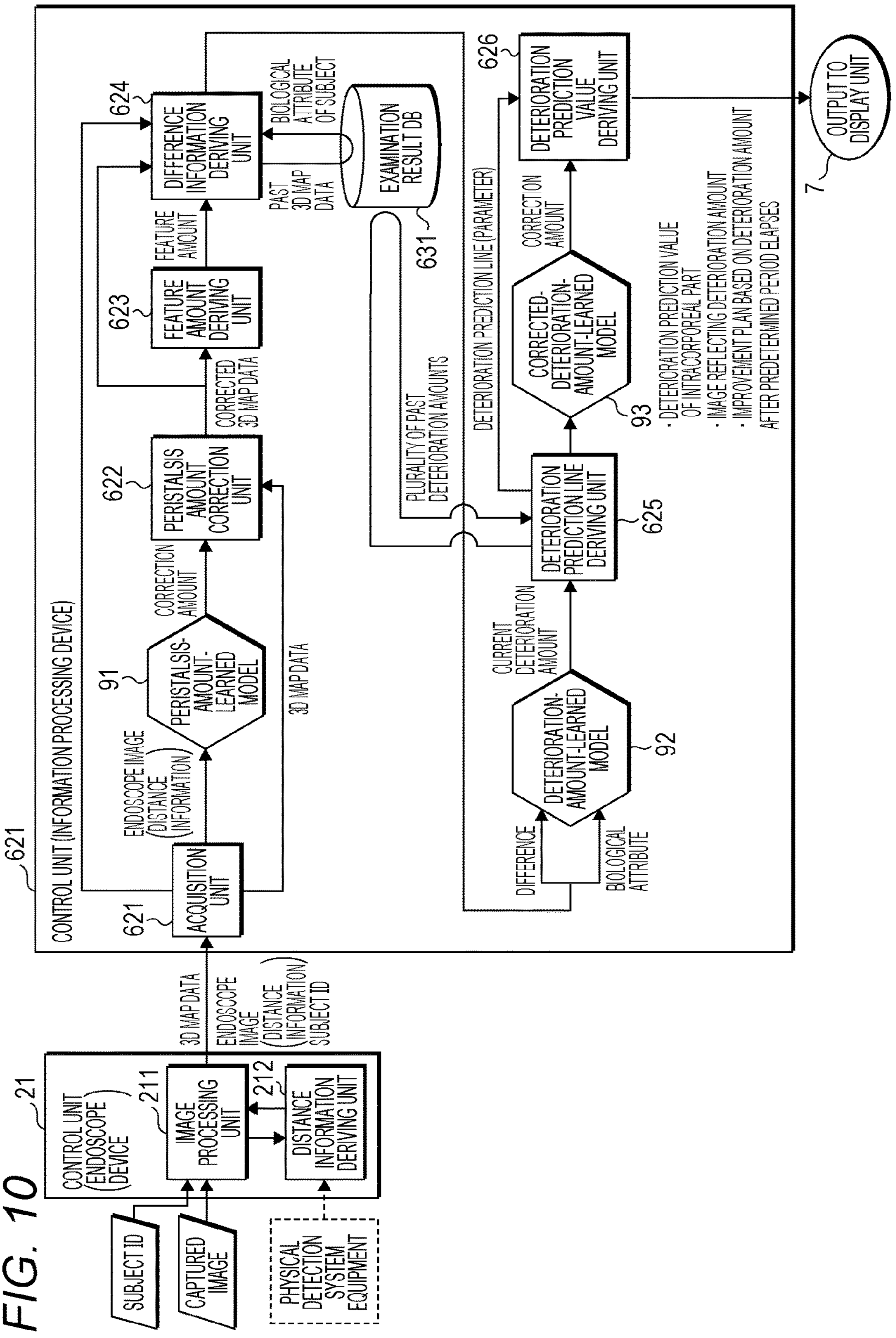

FIG. 10 is a functional block diagram illustrating functional parts included in the control unit 62 of the information processing apparatus 6 or the like. The control unit 21 of the processor 20 for an endoscope (endoscope device 10) executes the program P stored in the main storage device 22 to function as the image processing unit 211 and the distance information deriving unit 212. The control unit 62 of the information processing apparatus 6 executes the program P stored in the storage unit 63 to function as an acquisition unit 621, a peristalsis amount correction unit 622, a feature amount deriving unit 623, a difference information deriving unit 624, a deterioration prediction line deriving unit 625, and a deterioration prediction value deriving unit 626. In addition, the control unit 62 executes the program P stored in the storage unit 63 or reads an entity file constituting a learned model such as the peristalsis-amount-learned model 91 to function as the peristalsis-amount-learned model 91, the deterioration-amount-learned model 92, and the corrected-deterioration-amount-learned model 93.

The distance information deriving unit 212 derives information on a distance from the image sensor (the image sensor provided at the distal tip 443) to the intracorporeal part (organ inner wall) on the basis of the endoscope image or the captured image.

The image processing unit 211 performs various types of image processing such as gamma correction, white balance correction, and shading correction on an image (captured image) output from the endoscope, and outputs the image as the endoscope image. In addition, the image processing unit 211 further acquires the distance information derived by the distance information deriving unit 212, performs three-dimensional texture mapping on the basis of the distance information and an image subjected to the transformation processing, and generates the three-dimensional map data. The image processing unit 211 outputs (transmits) the acquired or generated captured image, endoscope image, distance information, and three-dimensional map data to the information processing apparatus 6. The image processing unit 211 may superimpose the distance information on the endoscope image or the captured image and output the endoscope image or the captured image on which the distance information is superimposed to the information processing apparatus 6. The image processing unit 211 further outputs the subject ID input from the keyboard 15 to the information processing apparatus 6.

The acquisition unit 621 acquires the endoscope image, the captured image, the distance information, the three-dimensional map data, and the subject ID output by the processor 20 for an endoscope, outputs the acquired endoscope image and the distance information (or the endoscope image on which the distance information is superimposed) to the peristalsis-amount-learned model 91, and outputs the three-dimensional map data to the peristalsis amount correction unit 622. The acquisition unit 621 outputs the acquired subject ID to the difference information deriving unit 624.

The peristalsis-amount-learned model 91 inputs the endoscope image and the distance information output from the acquisition unit 621 to the input layer, and outputs the correction amount for the peristalsis amount output from the output layer to the peristalsis amount correction unit 622.

The peristalsis amount correction unit 622 corrects the three-dimensional map data output from the acquisition unit 621 on the basis of the peristalsis amount correction amount output from the peristalsis-amount-learned model 91. Since the three-dimensional map data is corrected on the basis of the correction amount for the peristalsis amount, distance change noise caused by peristalsis can be canceled (removed). The peristalsis amount correction unit 622 outputs the corrected three-dimensional map data to the feature amount deriving unit 623 and the difference information deriving unit 624.

The feature amount deriving unit 623 derives, for example, a feature amount for specifying an intracorporeal part suspected of being a lesion from the surface shape, color information, and the like of the three-dimensional map data corrected by the peristalsis amount correction unit 622, and outputs the derived feature amount to the difference information deriving unit 624. The feature amount deriving unit 623 may derive a plurality of feature amounts from the three-dimensional map data.

The difference information deriving unit 624 acquires three-dimensional map data that is a past (previous) examination result of the corresponding subject ID by referring to the examination result DB 631 on the basis of the acquired subject ID. The difference information deriving unit 624 performs superimposition processing on the three-dimensional map data acquired from the peristalsis amount correction unit 622 and the previous three-dimensional map data on the basis of the acquired feature amount, and derives difference information including feature amount difference values of the shape, and saturation, hue, and luminosity in a color space of the surface of the organ (intracorporeal part). The difference information deriving unit 624 outputs the derived difference information and information regarding the biological attribute such as the age of the subject specified by the subject ID to the deterioration-amount-learned model 92.

The deterioration-amount-learned model 92 inputs the difference information output from the difference information deriving unit 624 and the information on the biological attribute such as the age specified by the subject ID to the input layer, and outputs the deterioration amount (the deterioration amount in the current examination) output from the output layer to the deterioration prediction line deriving unit 625.

The deterioration prediction line deriving unit 625 acquires a plurality of deterioration amounts in the past examinations performed on the subject by referring to the examination result DB 631 on the basis of the subject ID. The deterioration prediction line deriving unit 625 derives a deterioration prediction line on the basis of the current deterioration amount and the plurality of past deterioration amounts that are acquired. For example, when deriving the deterioration prediction line as a straight line (linear approximation), the deterioration prediction line deriving unit 625 may use a least squares method on the basis of the current deterioration amount and the plurality of past deterioration amounts that are acquired. Alternatively, the deterioration prediction line deriving unit 625 may derive the deterioration prediction line by using various methods such as a logarithmic approximation curve, a polynomial approximation curve, a power approximation curve, or an exponential approximation curve. The deterioration prediction line deriving unit 625 outputs the derived deterioration prediction line (the parameter of the deterioration prediction line) to the corrected-deterioration-amount-learned model 93 and the deterioration prediction value deriving unit 626.

The corrected-deterioration-amount-learned model 93 inputs the deterioration prediction line (the parameter of the deterioration prediction line) output from the deterioration prediction line deriving unit 625 to the input layer, and outputs the correction amount output from the output layer to the deterioration prediction value deriving unit 626. The derivation of the correction amount is not limited to the case of using the corrected-deterioration-amount-learned model 93, and may be derived on the basis of, for example, the biological attribute such as age of the subject, and physical condition information such as a body temperature or heart rate at the time of examination. That is, a correction coefficient determined on the basis of the biological attribute and the physical condition information is stored in, for example, a table form in the storage unit 63, and the information processing apparatus 6 (control unit 62) derives the correction coefficient on the basis of the biological attribute or physical condition information of the subject acquired from the examination result DB 631, the processor 20 for an endoscope, or the like. Then, the information processing apparatus 6 may correct the parameter of the deterioration prediction line on the basis of the derived correction coefficient.

The deterioration prediction value deriving unit 626 corrects the deterioration prediction line output by the deterioration prediction line deriving unit 625 on the basis of the correction amount output by the corrected-deterioration-amount-learned model 93. The deterioration prediction value deriving unit 626 derives one or more future deterioration amounts (deterioration amount prediction values) after a predetermined period elapses from the current time point on the basis of the corrected deterioration prediction line. The deterioration prediction value deriving unit 626 outputs information including the derived deterioration amount prediction value to the display unit 7 such as a display. On the basis of the deterioration amount prediction value, the deterioration prediction value deriving unit 626 may derive the diagnosis support information such as an image obtained by visualizing the deterioration prediction value, or warning information or improvement proposal information determined on the basis of the deterioration prediction value, and output the diagnosis support information to the display unit 7, such that this information is displayed on the display unit 7.

In the present embodiment, the respective functional parts in the series of processing have been described separately as each functional part of the control unit 21 of the processor 20 for an endoscope and each functional part of the control unit 62 of the information processing apparatus 6, but the sharing of these functional parts is an example and is not limited thereto. The control unit 21 of the processor 20 for an endoscope may function as all functional parts implemented by the control unit 62 of the information processing apparatus 6 including the learned model such as the peristalsis-amount-learned model 91. That is, the processor 20 for an endoscope may substantially include the information processing apparatus 6. Alternatively, the control unit 21 of the processor 20 for an endoscope may only output the captured image captured by the image sensor, and the control unit 62 of the information processing apparatus 6 may function as all functional parts that perform the following processing. Alternatively, the control unit 21 of the processor 20 for an endoscope and the control unit 62 of the information processing apparatus 6 may function as respective functional parts in a series of processing in cooperation by performing inter-process communication, for example.

Figure 11:
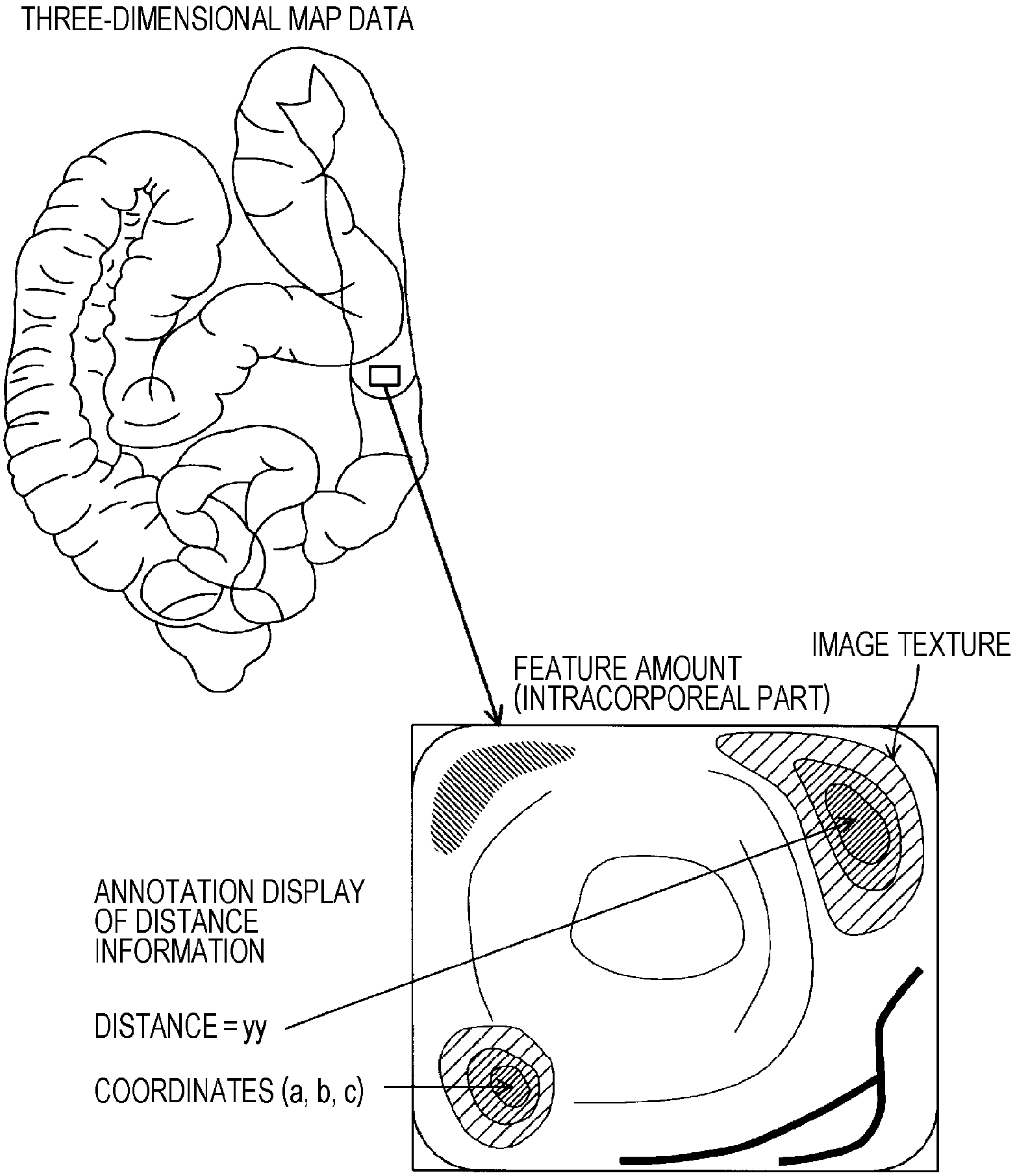
FIG. 11 is an explanatory diagram regarding three-dimensional map data generated on the basis of an image obtained by capturing an intracorporeal part.

FIG. 11 is an explanatory diagram regarding three-dimensional map data generated on the basis of an image obtained by capturing an intracorporeal part. As described above, the control unit 21 of the processor 20 for an endoscope generates the three-dimensional map data on the basis of the captured image or the endoscope image, and the information on the distance from the image sensor to the organ inner wall. A display screen including the generated three-dimensional map data is displayed on the display device of the endoscope device 10 or the display unit 7 of the information processing apparatus 6.

For the three-dimensional map data, for example, three-dimensional texture mapping reflecting the inner diameter of the body cavity is performed by superimposing the distance information and the feature amount extracted from the captured image or endoscope image including the surface of the organ. Furthermore, the distance information including the distance (the distance from the image sensor) or the position (the coordinates on the three-dimensional map) of the surface of the organ specified on the basis of the feature amount may be annotation-displayed on the three-dimensional map data.

Figure 12:
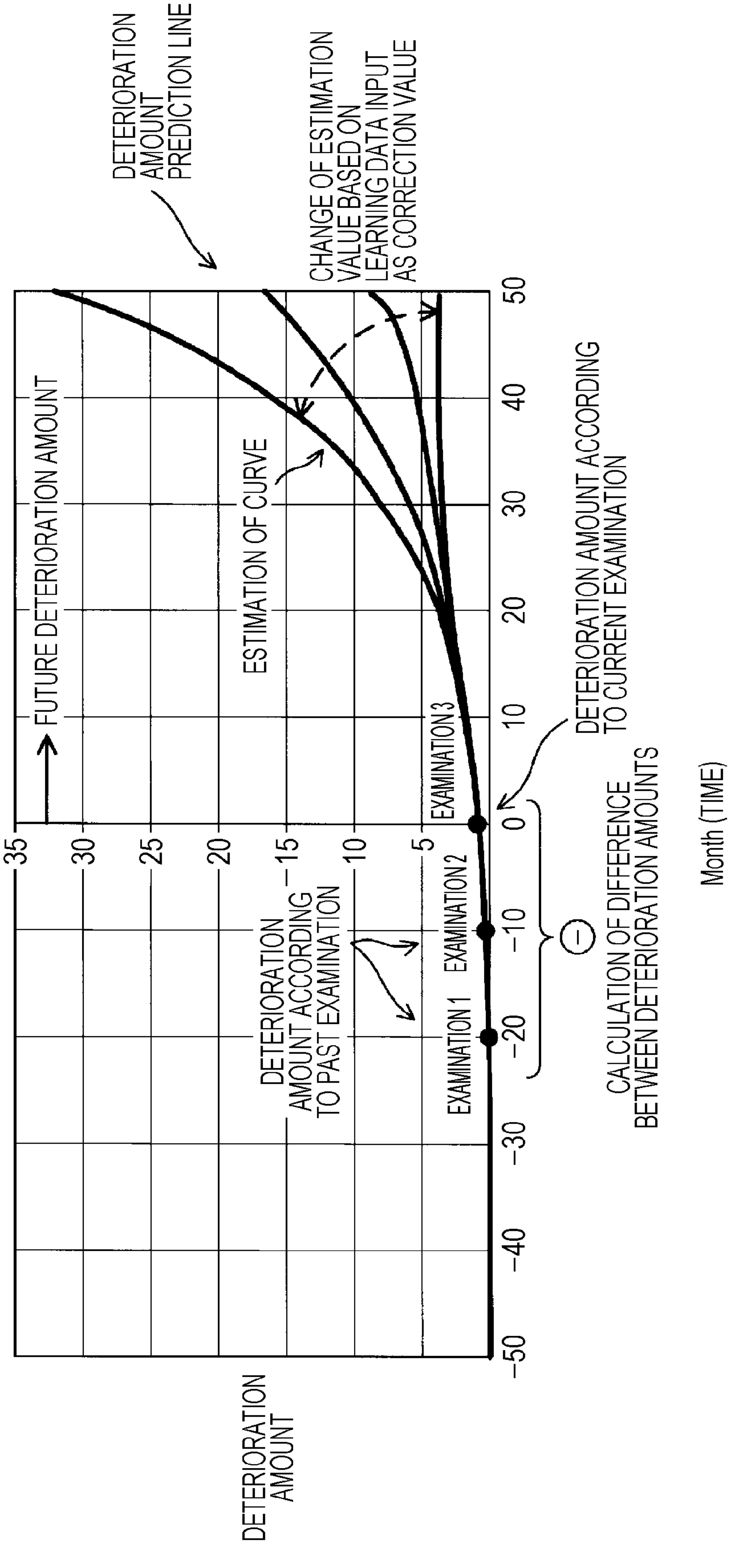
FIG. 12 is an explanatory diagram regarding a graph showing the deterioration estimation line.

FIG. 12 is an explanatory diagram regarding a graph showing the deterioration estimation line. As described above, the deterioration prediction value deriving unit 626 corrects the deterioration estimation line derived by the deterioration prediction line deriving unit 625 on the basis of the correction amount output from the corrected-deterioration-amount-learned model 93, and derives the corrected deterioration estimation line.

The horizontal axis of the graph showing the deterioration estimation line represents time, and the vertical axis indicates values of the current and past deterioration amounts and the future deterioration amount (deterioration prediction value). As illustrated in the drawing, three deterioration amounts are plotted on the basis of the past and current examinations. On the basis of the past and current deterioration amounts, an approximate line indicating the future deterioration amount (deterioration prediction value) is displayed as the deterioration prediction line.

As described above, the estimated value of the deterioration prediction line is changed on the basis of the correction amount output from the corrected-deterioration-amount-learned model 93. The correction amount is derived on the basis of, for example, the information regarding the biological attributes such as the age of the subject, and the corrected-deterioration-amount-learned model 93 also inputs the information regarding the biological attributes to the input layer, such that the accuracy of the future deterioration amount can be improved. The deterioration prediction value deriving unit 626 can derive deterioration amounts (the deterioration amounts at a plurality of future time points) at one or more time points after a predetermined period elapses from the current time point (the time point of the current examination) on the basis of the derived deterioration prediction line (corrected deterioration prediction line).

Figure 13:
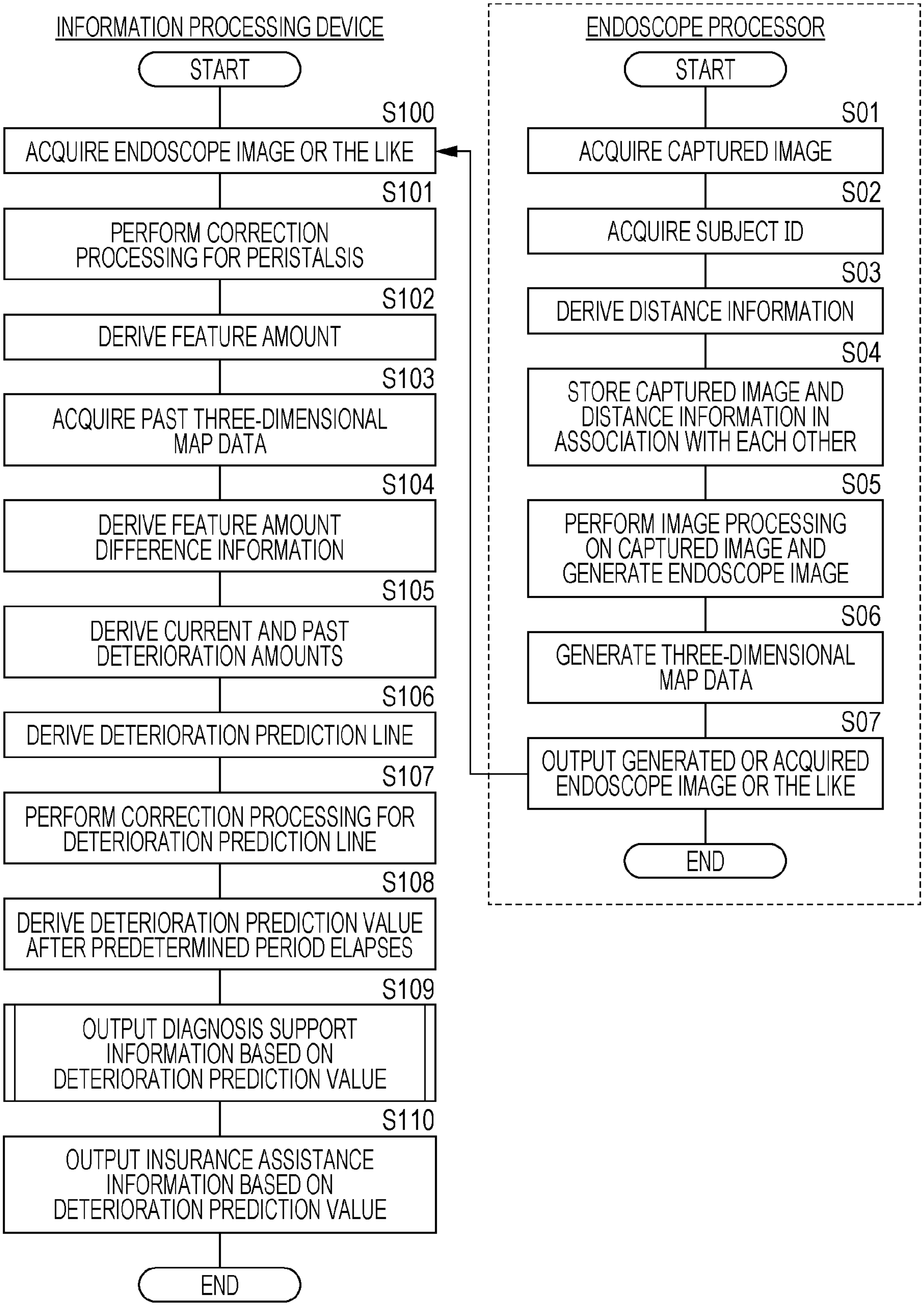
FIG. 13 is a flowchart illustrating an example of a processing procedure performed by the control unit of the information processing apparatus.
Figure 14:
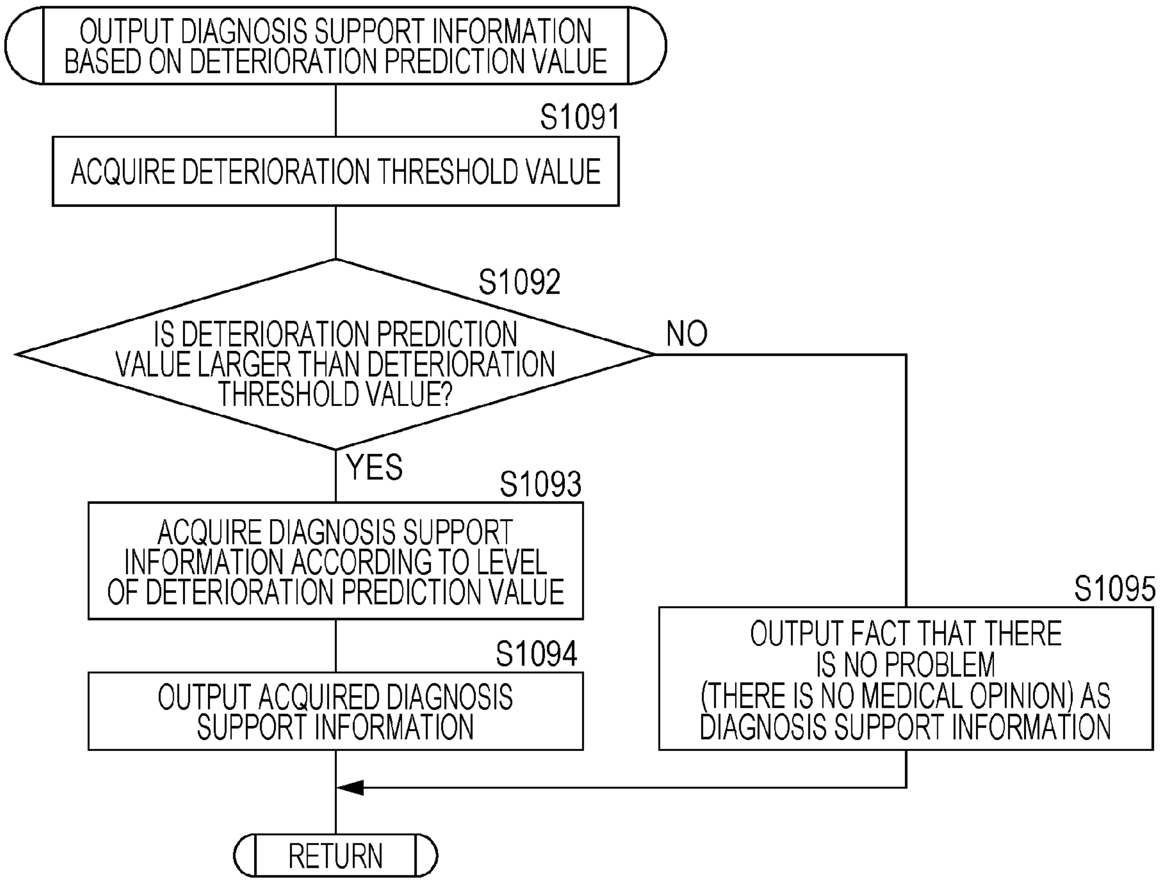
FIG. 14 is a flowchart illustrating an example of a processing procedure for deriving diagnosis support information, performed by the control unit of the information processing apparatus.

FIG. 13 is a flowchart illustrating an example of a processing procedure performed by the control unit 62 of the information processing apparatus 6. FIG. 14 is a flowchart illustrating an example of a processing procedure for deriving the diagnosis support information, performed by the control unit 62 of the information processing apparatus 6. For example, the information processing apparatus 6 starts the processing of the flowchart on the basis of a content input through the input unit 8 connected to the information processing apparatus 6 itself. The flowchart in the present embodiment includes processing performed by the processor 20 for an endoscope, which is a prerequisite processing when the information processing apparatus 6 acquires the endoscope image or the like from the endoscope device 10 (the processor 20 for an endoscope).

The control unit 62 of the processor 20 for an endoscope acquires the captured image output from the image sensor (S01). The control unit 62 of the processor 20 for an endoscope acquires the subject ID input from the keyboard 15 (S02).

The control unit 62 of the processor 20 for an endoscope derives the information on the distance from the image sensor to an image capturing target surface (intracorporeal part) (S03). In deriving the distance information, the control unit 62 of the processor 20 for an endoscope may further acquire detection result data output from the physical detection device and acquire the distance information on the basis of the detection result data and the captured image. The control unit 62 of the processor 20 for an endoscope stores the captured image and the distance information in association with each other (S04).

The control unit 62 of the processor 20 for an endoscope performs image processing on the captured image to generate the endoscope image (S05). The control unit 62 of the processor 20 for an endoscope performs various types of image processing such as affine transformation, projective transformation, gamma correction, white balance correction, and shading correction, and generates the endoscope image whose visibility for the operator is improved.

The control unit 62 of the processor 20 for an endoscope generates the three-dimensional map data (S06). The control unit 62 of the processor 20 for an endoscope performs the three-dimensional texture mapping reflecting the inner diameter of the body cavity. The control unit 62 of the processor 20 for an endoscope may perform the three-dimensional texture mapping by superimposing the distance information related to the target intracorporeal part and the feature amount extracted from the endoscope image including the surface of the organ. When performing the three-dimensional texture mapping, the control unit 62 of the processor 20 for an endoscope may perform interpolation by using detection data from the physical detection device described above.

The control unit 62 of the processor 20 for an endoscope outputs the generated or acquired distance information, endoscope image, three-dimensional map data, and subject ID, and transmits them to the information processing apparatus 6 (S07). The control unit 62 of the processor 20 for an endoscope may further output the captured image captured by the image sensor and transmit the captured image to the information processing apparatus 6. The control unit 62 of the processor 20 for an endoscope may superimpose the distance information on the endoscope image and transmit the endoscope image on which the distance information is superimposed to the information processing apparatus 6.

The control unit 62 of the information processing apparatus 6 acquires the endoscope image or the like output from the processor 20 for an endoscope (S100). The control unit 62 acquires the captured image, the endoscope image (the endoscope image on which the distance information is superimposed), the three-dimensional map data, and the subject ID output from the processor 20 for an endoscope. The control unit 62 may store the acquired captured image, endoscope image, three-dimensional map data, and subject ID in the examination result DB 631.

The control unit 62 of the information processing apparatus 6 performs peristalsis correction processing on the three-dimensional map data (S101). The control unit 62 inputs the endoscope image (the distance information and the endoscope image) on which the distance information is superimposed to the peristalsis-amount-learned model 91, and performs peristalsis correction processing such as correcting the arrangement of the surface of the organ wall in the vertical direction on the three-dimensional map data on the basis of the correction amount output by the peristalsis-amount-learned model 91.

The control unit 62 of the information processing apparatus 6 derives the feature amount from the corrected three-dimensional map data (S102). The control unit 62 derives the feature amount from the surface shape, color information, or the like of the corrected three-dimensional map data. By using the three-dimensional map data, it is possible to digitize the surface shape, the color information, or the like of the intracorporeal part, reduce the arithmetic operation load for deriving the feature amount, and efficiently derive the feature amount.

The control unit 62 of the information processing apparatus 6 acquires the past three-dimensional map data by referring to the examination result DB 631 on the basis of the acquired subject ID (S103). The control unit 62 of the information processing apparatus 6 performs the superimposition processing on the current and past three-dimensional map data to derive the difference information of the feature amounts in the three-dimensional map data (S104). By using the three-dimensional map data, the information regarding the feature amount in the intracorporeal part is digitized, and the difference processing is performed by using each digitized value, such that the difference information can be efficiently derived.

The control unit 62 of the information processing apparatus 6 derives the current and past deterioration amounts on the basis of the difference information and the biological attribute (S105). The control unit 62 inputs the derived difference information and the biological attribute acquired by searching the examination result DB 631 with the subject ID to the deterioration-amount-learned model 92, and acquires the deterioration amount (the current deterioration amount) output by the deterioration-amount-learned model 92. In addition, the control unit 62 searches the examination result DB 631 with the subject ID to acquire the past deterioration amount of the subject. The control unit 62 derives the current and past deterioration amounts by acquiring them from the deterioration-amount-learned model 92 and the examination result DB 631 in this manner.

The control unit 62 of the information processing apparatus 6 derives the deterioration prediction line on the basis of the current and past deterioration amounts (S106). The control unit 62 derives the deterioration prediction line by using a linear approximation or a nonlinear approximation method on the basis of each of the current and past deterioration amounts.

The control unit 62 of the information processing apparatus 6 performs deterioration prediction line correction processing (S107). The control unit 62 inputs the derived deterioration prediction line (the parameter of the deterioration prediction line) to the corrected-deterioration-amount-learned model 93, and acquires the correction amount for the deterioration prediction line output by the corrected-deterioration-amount-learned model 93. The control unit 62 performs the deterioration prediction line correction processing on the derived deterioration prediction line (the parameter of the deterioration prediction line) on the basis of the correction amount acquired from the corrected-deterioration-amount-learned model 93. Alternatively, the correction coefficient determined on the basis of the biological attribute and the physical condition information of the subject may be stored in, for example, a table form (correction coefficient table) in the storage unit 63, and the control unit 62 may derive the correction coefficient for correcting the deterioration prediction line by referring to the correction coefficient table stored in the storage unit 63. That is, the control unit 62 may derive the correction coefficient by referring to the correction coefficient table on the basis of the biological attribute or physical condition information of the subject acquired from the examination result DB 631, the processor 20 for an endoscope, or the like, and perform the correction processing for the deterioration prediction line (the parameter of the deterioration prediction line) by using the correction coefficient. The correction coefficient used for the deterioration prediction line (the parameter of the deterioration prediction line) may be variable according to the elapsed time from the current time point with respect to each time point in the future predicted by the deterioration prediction line. That is, the correction coefficient includes the elapsed time from the current time point as a variable (time variable), and the value of the correction coefficient may be changed according to the elapsed time from the current time point to correct the deterioration prediction line (the parameter of the deterioration prediction line). For example, as compared with a correction coefficient (k1) in a case of targeting a time point in the near future from the current time point, a correction coefficient (k2) in a case of targeting a time point later than the corresponding time point may be set to be smaller, such that the degree of influence of the correction coefficient is reduced as the elapsed time from the current time point becomes longer to thereby narrow the error range.

The control unit 62 of the information processing apparatus 6 derives the deterioration prediction value after a predetermined period elapses (S108). The control unit 62 derives the deterioration prediction value at one or more time points after a predetermined period elapses from the current time point (a time point of the current examination) on the basis of the corrected deterioration prediction line.

The control unit 62 of the information processing apparatus 6 outputs the diagnosis support information (notification information) on the basis of the deterioration prediction value (S109). On the basis of the deterioration prediction value, the control unit 62 derives, as the notification information, the diagnosis support information such as an image obtained by visualizing the deterioration prediction value, warning information determined on the basis of the deterioration prediction value, or improvement proposal information, outputs the notification information, and displays the notification information on the display unit 7. The storage unit 63 stores, for example, a diagnosis support DB (not illustrated) in which the warning information, improvement proposal information, or the like is associated with the deterioration prediction value and the biological attribute, and the control unit 62 derives the warning information, improvement proposal information, or the like determined on the basis of the deterioration prediction value by referring to the diagnosis support DB. The diagnosis support information such as the warning information, improvement proposal information, or the like determined on the basis of the deterioration prediction value may be derived by comparing the predicted deterioration prediction value with a predetermined deterioration threshold value. In a case where the predicted deterioration prediction value is smaller than the deterioration threshold value, the control unit 62 may derive, as the diagnosis support information, information indicating that there is no problem, such as information indicating that there is no medical opinion. In performing the processing of S109, the control unit 62 derives the diagnosis support information according to the flow of the processing in the flowchart illustrated in FIG. 14.

The control unit 62 of the information processing apparatus 6 acquires the deterioration threshold value (S1091). The deterioration threshold value is stored in, for example, a table form in the storage unit 63 of the information processing apparatus 6, in association with the information regarding the biological attribute such as the age or sex of the subject, and a target intracorporeal part. Further, the deterioration threshold value may include a plurality of deterioration threshold values based on a plurality of stages, that is, lesion stages. As an example, the greater the value of the deterioration threshold value, the higher the lesion severity stage. For example, the control unit 62 acquires the deterioration threshold value by deriving the deterioration threshold value with reference to the storage unit 63 on the basis of the biological attribute such as the age or sex of the subject and the target intracorporeal part corresponding to the deterioration amount.

The control unit 62 of the information processing apparatus 6 determines whether or not the deterioration prediction value is larger than the deterioration threshold value (S1092). As described above, in a case where the deterioration threshold value includes a plurality of deterioration threshold values based on the lesion stages, the control unit 62 compares the deterioration threshold value (minimum deterioration threshold value) having the smallest value with the deterioration prediction value, and determines whether or not the deterioration prediction value is larger than the deterioration threshold value (minimum deterioration threshold value).

In a case where the deterioration prediction value is larger than the deterioration threshold value (minimum deterioration threshold value) (S1092: YES), the control unit 62 of the information processing apparatus 6 acquires diagnosis support information corresponding to the level of the deterioration prediction value (S1093). In a case where the deterioration threshold value includes a plurality of deterioration threshold values based on the lesion stages, the control unit 62 specifies a deterioration threshold value closest to the deterioration prediction value among the plurality of deterioration threshold values based on the lesion stages. Each of the plurality of deterioration threshold values is associated with each lesion stage, and the control unit 62 specifies a lesion stage corresponding to the deterioration prediction value corresponding to the level of the deterioration threshold value on the basis of the specified deterioration threshold value. Alternatively, the control unit 62 may specify the lesion stage corresponding to the deterioration prediction value on the basis of a range to which the deterioration prediction value belongs among respective ranges determined by the plurality of deterioration threshold values based on the lesion stages.

The storage unit 63 of the information processing apparatus 6 stores the diagnosis support information corresponding to each lesion stage. For example, the diagnosis support information in a case where the lesion stage is mild is improvement proposal information for encouraging regular exercise. The diagnosis support information in a case where the lesion stage is moderate is recommendation information indicating that a thorough examination is required. The diagnosis support information in a case where the lesion stage is severe is warning information suggesting hospital treatment or the like.

The control unit 62 of the information processing apparatus 6 outputs the acquired diagnosis support information (S1094). The control unit 62 outputs the diagnosis support information such as the improvement proposal information, recommendation information, or warning information corresponding to each lesion stage.

In a case where the deterioration prediction value is not larger than the deterioration threshold value (minimum deterioration threshold value), that is, in a case where the deterioration prediction value is equal to or smaller than the deterioration threshold value (minimum deterioration threshold value) (S1092: NO), the control unit 62 of the information processing apparatus 6 outputs, as the diagnosis support information, information indicating that there is no problem (there is no medical opinion) (S1095).

The control unit 62 of the information processing apparatus 6 outputs insurance support information on the basis of the deterioration prediction value (S110). The control unit 62 derives insurance support information such as an insurance grade or an estimated insurance premium on the basis of the deterioration prediction value, and displays the insurance support information on the display unit 7. For example, an insurance support DB (not illustrated) in which the insurance grade, the estimated insurance premium, or the like is associated with the deterioration prediction value and the biological attribute is stored in the storage unit 63, and the control unit 62 derives the insurance grade, the estimated insurance premium, or the like determined on the basis of the deterioration prediction value by referring to the insurance support DB.

In the present embodiment, the derivation of the feature amount in the captured intracorporeal part is performed by using the three-dimensional map data, but the present invention is not limited thereto. The control unit 62 may derive the feature amount on the basis of the endoscope image or the captured image acquired from the processor 20 for an endoscope.

Figure 15:
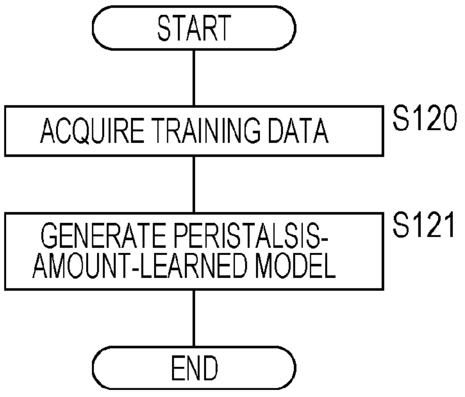
FIG. 15 is a flowchart illustrating an example of a processing procedure regarding processing of generating the peristalsis-amount-learned model, performed by the control unit of the information processing apparatus.

FIG. 15 is a flowchart illustrating an example of a processing procedure regarding processing of generating the peristalsis-amount-learned model 91, performed by the control unit 62 of the information processing apparatus 6. The control unit 62 of the information processing apparatus 6 acquires the training data (S120). As described above, the training data has the endoscope image and the distance information as the problem data and has the correction amount for the peristalsis amount as the answer data, and is data in which the correction amount for the peristalsis amount is labeled for the endoscope image and the distance information. The correction amount for the peristalsis amount labeled in the endoscope image and the distance information may be, for example, the amount specified on the basis of determination regarding how the peristalsis of an imaged portion (intracorporeal part) in the endoscope image occurs and whether or not the peristalsis is a normal physiological response based on the periodicity of a distance change in the distance information, the determination being made by a doctor or the like. The endoscope image and the distance information, which are original data of such training data, are stored in a large amount as the result data of the endoscopic examination performed in each medical institution, and it is possible to generate a large amount of training data for training the peristalsis-amount-learned model 91, by using these result data.

The control unit 62 of the information processing apparatus 6 generates the peristalsis-amount-learned model 91 (S121). The control unit 62 constructs (generates) the peristalsis-amount-learned model 91 that receives the endoscope image and distance information and outputs the correction amount for the peristalsis amount, by using the acquired training data. In a case where the peristalsis-amount-learned model 91 is a neural network, the parameter used for the arithmetic processing in the intermediate layer is optimized by using, for example, backpropagation. Similarly to the peristalsis-amount-learned model 91, the control unit 62 of the information processing apparatus 6 acquires training data corresponding to each of the deterioration-amount-learned model 92 and the corrected-deterioration-amount-learned model 93, and generates each learned model.

According to the present embodiment, the information processing apparatus 6 acquires a plurality of images captured by the endoscope over a predetermined period, and estimates the future state of an intracorporeal part included in the plurality of images on the basis of the plurality of acquired images and the like. Therefore, since the future state of a predetermined intracorporeal part of the subject is estimated on the basis of a plurality of images captured by the endoscope over a predetermined period and including the intracorporeal part, diagnosis support regarding the future change of the target part of the subject can be performed. Note that the image acquired by the information processing apparatus 6 is not limited to the captured image captured by the image sensor, and includes the endoscope image obtained by performing image processing on the captured image or the three-dimensional model data generated on the basis of the captured image and distance information from the image sensor.

According to the present embodiment, the information processing apparatus 6 estimates a plurality of states of the intracorporeal part included in the plurality of acquired images for each predetermined elapsed period in the future. Therefore, by the estimation, information regarding the future development of the lesion in the intracorporeal part can be provided for the diagnosis support.

According to the present embodiment, the information processing apparatus 6 outputs the notification information (diagnosis support information) on the basis of the estimated future state of the intracorporeal part. Since the information processing apparatus 6 outputs, on the basis of the estimated future state of the intracorporeal part, the notification information (diagnosis support information) including, for example, an attention attracting degree according to the stage of the lesion in the state, the information processing apparatus 6 can output information contributing to making the diagnosis support more efficient.

According to the present embodiment, the information processing apparatus 6 derives difference data based on the respective images included in the plurality of images, that is, data regarding the amount of change between the respective images, and estimates the future state of the intracorporeal part on the basis of the difference data, such that the estimation accuracy can be improved.

According to the present embodiment, the information processing apparatus 6 generates the three-dimensional map data on the basis of the distance information and the image of the intracorporeal part, and estimates the future state of the intracorporeal part on the basis of the three-dimensional map data, such that the estimation accuracy can be improved by using numerical information in the distance information.

According to the present embodiment, the information processing apparatus 6 derives, on the basis of the acquired image, the information regarding the peristalsis of the intracorporeal part included in the image, and corrects, for example, the arrangement of the surface of the organ wall in the vertical direction in the three-dimensional map data on the basis of the information regarding the peristalsis of the intracorporeal part, such that it is possible to remove a noise component caused by the peristalsis of the intracorporeal part and improve the estimation accuracy. Since the information processing apparatus 6 uses the peristalsis-amount-learned model 91 in performing the correction, the correction accuracy can be improved.

According to the present embodiment, the information processing apparatus 6 derives the deterioration amount of the intracorporeal part on the basis of the three-dimensional map data generated from each of the plurality of images. In deriving the deterioration amount, the information processing apparatus 6 performs superimposition processing on the three-dimensional map data in the current examination and the three-dimensional map data of the previous result (the past examination), and derives a feature amount difference value (difference information) of the shape, saturation, or the like of the intracorporeal part (the surface of the organ). Since the information processing apparatus 6 inputs the difference information to the deterioration-amount-learned model 92 to acquire the deterioration amount, the accuracy of the derived deterioration amount can be improved. Furthermore, since the information processing apparatus 6 estimates the future state of the intracorporeal part on the basis of the deterioration prediction line generated by using the derived deterioration amount, the estimation accuracy can be improved.

According to the present embodiment, since the information processing apparatus 6 corrects the derived deterioration amount on the basis of the information regarding the biological attribute of the subject, the estimation accuracy can be improved. The biological attribute includes, for example, information regarding the biological attribute such as the age or sex of the subject. Since the information processing apparatus 6 uses the corrected-deterioration-amount-learned model 93 in performing the correction, the correction accuracy can be improved.

Third Embodiment

Figure 16:
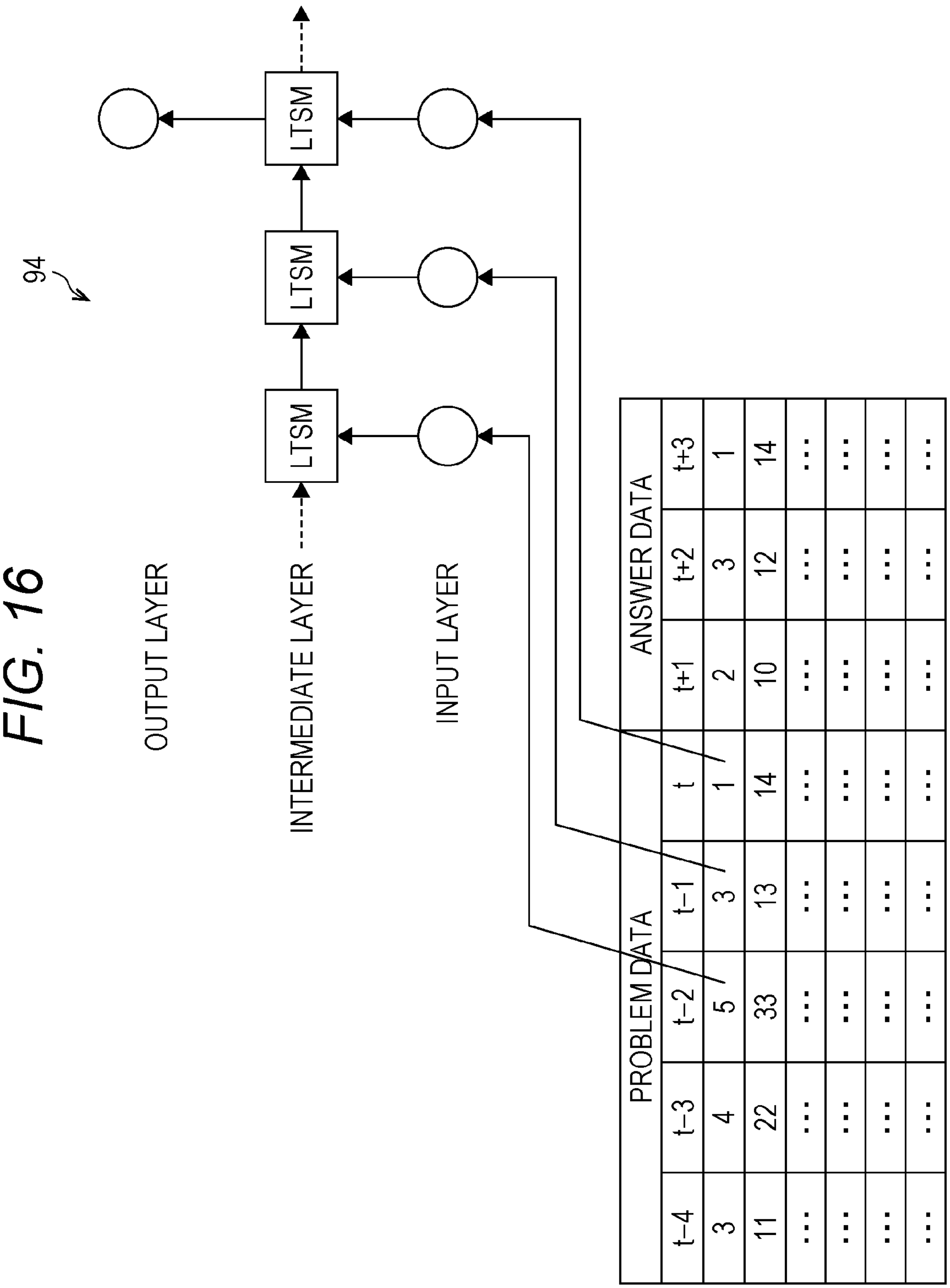
FIG. 16 is an explanatory diagram regarding processing of generating a difference-learned model according to a third embodiment.

FIG. 16 is an explanatory diagram regarding processing of generating a difference-learned model 94 according to a third embodiment. The information processing apparatus 6 constructs (generates) a neural network that receives a plurality of time-series difference information and outputs difference information at a plurality of future time points by performing learning on the basis of training data having the plurality of time-series difference information as the problem data and having the difference information at a plurality of future time points as the answer data.

The plurality of time-series difference information means a plurality of time-series difference information on a predetermined intracorporeal part (an intracorporeal part specified on the basis of the feature amount extracted from the endoscope image) of the same subject, from the past to the current time point (a predetermined time point). The difference information at a plurality of future time points means difference information at a plurality of future time points such as the next time point after the current time point (a predetermined time point) and the one after the next time point. The difference information corresponds to the state (the quantity of state of the predetermined intracorporeal part) derived from the endoscope image.

The input layer has one or more neurons that receive the plurality of time-series difference information, and transfers each of the input difference information to the intermediate layer. The intermediate layer includes an autoregressive layer having a plurality of neurons. The autoregressive layer is implemented as, for example, a long short term memory (LSTM) model, and a neural network including such an autoregressive layer is referred to as a recurrent neural network (RNN). The intermediate layer outputs a change amount based on each of the plurality of difference information sequentially input in time series. The output layer has one or more neurons that receive the difference information at a plurality of future time points, and outputs the difference information at the plurality of future time points on the basis of the change amount based on each of the plurality of difference information output from the intermediate layer. Such learning for the RNN is performed by using, for example, a backpropagation through time (BPTT) algorithm.

The training data may be stored in an array. In a case where the training data is stored in an array, for example, the values of elements with numbers, 0 to 4 ($t-4$ to $t$), may be used as the problem data, and the values of elements with numbers, 5 to 7 ($t+1$ to $t+3$) may be used as the answer data. The time-series problem data ($t-2$, $t-1$, and $t$) input from the input layer are sequentially transferred to the LSTM (autoregressive layer), and the LSTM (autoregressive layer) can output the output value to the output layer and its own layer, thereby processing series information including the temporal change and the order.

Figure 17:
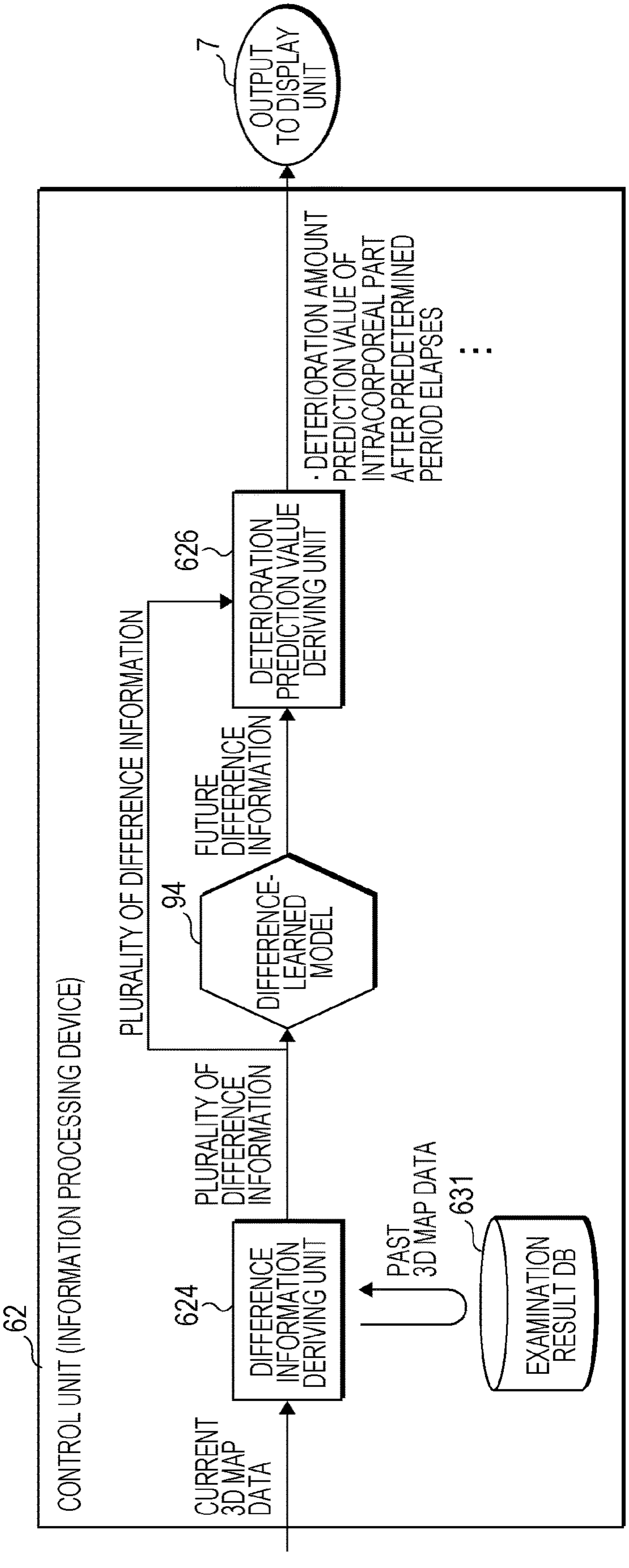

FIG. 17 is a functional block diagram illustrating functional parts included in the control unit 62 of the information processing apparatus 6 or the like. The control unit 62 executes the program P stored in the storage unit 63 to function as the difference information deriving unit 624. The control unit 62 executes the program P stored in the storage unit 63 or reads an entity file constituting the difference-learned model 94 to function as the difference-learned model 94.

Similarly to the second embodiment, the difference information deriving unit 624 performs superimposition processing on the three-dimensional map data acquired from the peristalsis amount correction unit 622 and the previous three-dimensional map data, and derives difference information (difference information of the current examination) including feature amount difference values of the shape, and saturation, hue, and luminosity in a color space of the surface of the organ (intracorporeal part).

The difference information deriving unit 624 acquires the three-dimensional map data in the past examination performed on the subject by referring to the examination result DB 631 on the basis of the subject ID, and derives difference information of the past examination on the basis of the acquired three-dimensional map data in the past examination.

The difference information deriving unit 624 generates a plurality of time-series difference information from the past to the current time point (the time point of the current examination) on the basis of the derived current and past difference information, and outputs the plurality of difference information to the difference-learned model 94 and the deterioration prediction value deriving unit 626.

The difference-learned model 94 inputs the plurality of time-series difference information to the input layer, and outputs difference information at a plurality of future time points output from the output layer to the deterioration prediction value deriving unit 626.

The deterioration prediction value deriving unit 626 derives a plurality of deterioration amounts from the past to the future on the basis of the acquired current and past difference information and the difference information at a plurality of future time points, and derives the deterioration prediction line on the basis of the plurality of deterioration amounts. In deriving the deterioration prediction line, the deterioration-amount-learned model 92 and the corrected-deterioration-amount-learned model 93 may be used as in the second embodiment. The deterioration prediction value deriving unit 626 derives the deterioration amount at one or more time points after a predetermined period elapses from the current time point (the time point of the current examination) on the basis of the derived deterioration prediction line as in the second embodiment. In addition, the deterioration prediction value deriving unit 626 may derive and output the diagnosis support information such as improvement proposal information on the basis of the derived future deterioration amount.

Figure 18:
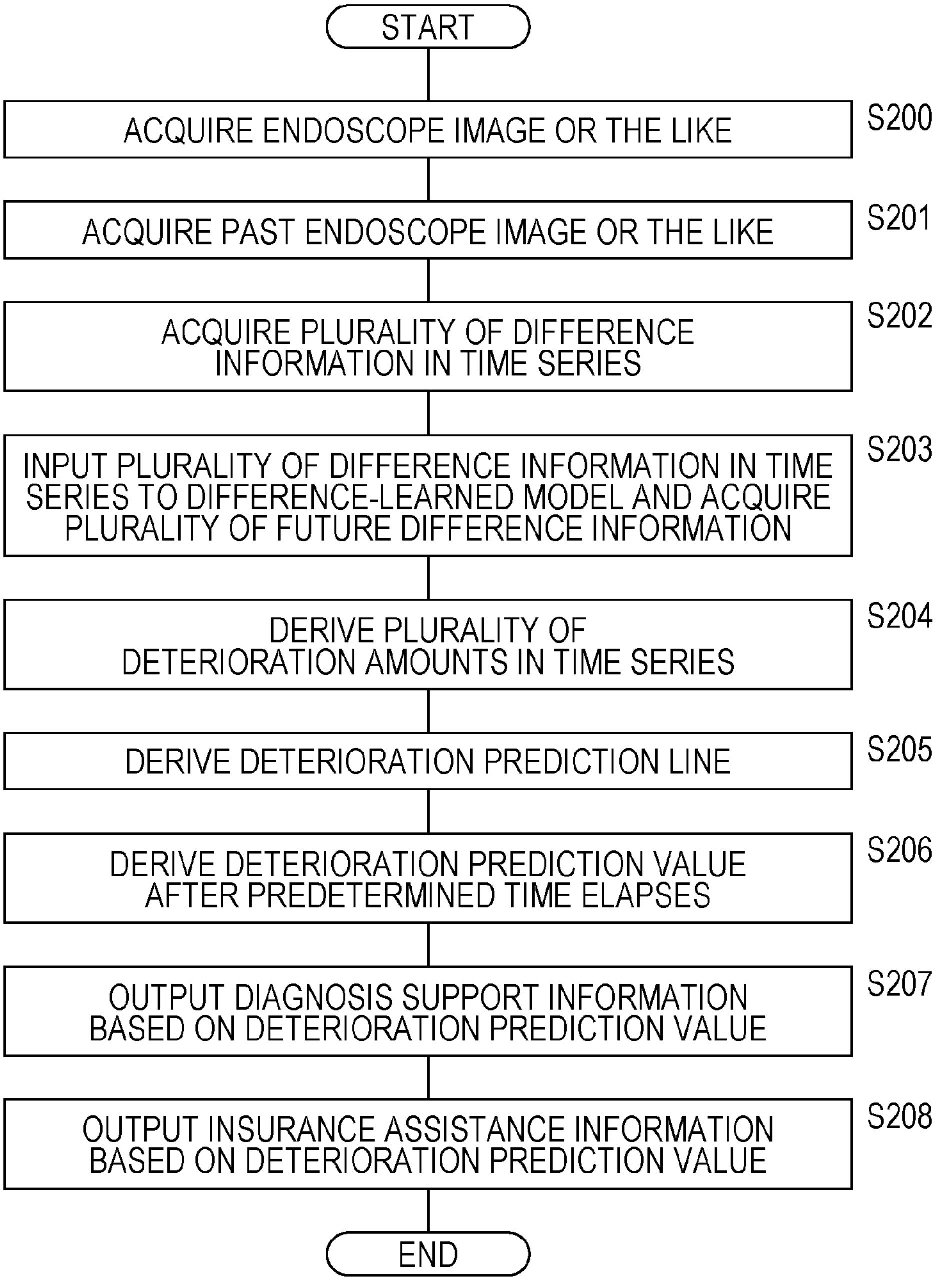
FIG. 18 is a flowchart illustrating an example of a processing procedure performed by the control unit of the information processing apparatus.

FIG. 18 is a flowchart illustrating an example of a processing procedure performed by the control unit 62 of the information processing apparatus 6. For example, the information processing apparatus 6 starts the processing of the flowchart on the basis of a content input through the input unit 8 connected to the information processing apparatus 6 itself.

The control unit 62 of the information processing apparatus 6 acquires the endoscope image or the like (S200). Similarly to the second embodiment, the control unit 62 acquires the endoscope image, the three-dimensional map data, and the subject ID from the endoscope device 10.

The control unit 62 of the information processing apparatus 6 acquires the past endoscope image or the like (S201). The control unit 62 acquires the past endoscope image and the three-dimensional map data of the subject by referring to the examination result DB 631 on the basis of the subject ID.

The control unit 62 of the information processing apparatus 6 acquires a plurality of time-series difference information on the basis of the current and past endoscope images or the like (S202). When acquiring the plurality of time-series difference information, the control unit 62 derives the difference information based on the three-dimensional map data adjacent in time series by performing superimposition processing on each of the three-dimensional map data generated from the endoscope image. Alternatively, the control unit 62 may derive the difference information on the basis of the endoscope image.

The control unit 62 of the information processing apparatus 6 inputs the plurality of time-series difference information to the difference-learned model 94 and acquires a plurality of future difference information (S203). The control unit 62 of the information processing apparatus 6 derives a plurality of time-series deterioration amounts on the basis of a plurality of past, current, and future difference states (S204). The control unit 62 derives a plurality of time-series deterioration amounts from the past to the future on the basis of the plurality of time-series difference information (the difference information from the past to the present) derived in the processing of S202 and the plurality of future difference information output by the difference-learned model 94.

The control unit 62 of the information processing apparatus 6 derives the deterioration prediction line (S205). The control unit 62 derives the deterioration prediction line by using a linear approximation or a curve approximation method on the basis of the plurality of time-series deterioration amounts from the past to the future.

The control unit 62 of the information processing apparatus 6 derives the deterioration prediction value after a predetermined period elapses (S206). The control unit 62 derives, on the basis of the deterioration prediction line, one or more deterioration prediction values after a predetermined period elapses in the future.

The control unit 62 of the information processing apparatus 6 outputs the diagnosis support information on the basis of the deterioration prediction value (S207). The control unit 62 of the information processing apparatus 6 outputs the insurance support information on the basis of the deterioration prediction value (S208). Similarly to the second embodiment, the control unit 62 outputs the diagnosis support information and the insurance support information on the basis of the deterioration prediction value.

According to the present embodiment, in a case where difference data derived from three-dimensional map data generated on the basis of a plurality of past images captured in time series by the endoscope is input, the information processing apparatus 6 can efficiently generate the difference-learned model 94 that outputs a plurality of time-series future difference data. Furthermore, the information processing apparatus 6 efficiently derives the future difference information by using the difference-learned model 94, and derives each deterioration amount on the basis of each of the derived difference information, such that the accuracy in estimating the future deterioration amount can be improved.

In the present embodiment, the state derived from the endoscope image (the quantity of state of the predetermined intracorporeal part) is described as being based on the difference information, but the present invention is not limited thereto. The state (the quantity of state of the predetermined intracorporeal part) derived from the endoscope image may also be based on the deterioration amount. The information processing apparatus 6 may construct (generate) a neural network (deterioration-amount-learned model) that receives a plurality of time-series deterioration amounts and outputs the deterioration amounts at a plurality of future time points by performing learning on the basis of training data having the plurality of time-series deterioration amounts as the problem data and having the deterioration amounts at the plurality of future time points as the answer data. The information processing apparatus 6 may input a deterioration amount derived from the plurality of acquired endoscope images to the deterioration-amount-learned model, acquire a plurality of time-series future deterioration amounts, and estimate the future state of the intracorporeal part included in the plurality of images on the basis of the plurality of acquired time-series future deterioration amounts.

Fourth Embodiment

Figure 19:
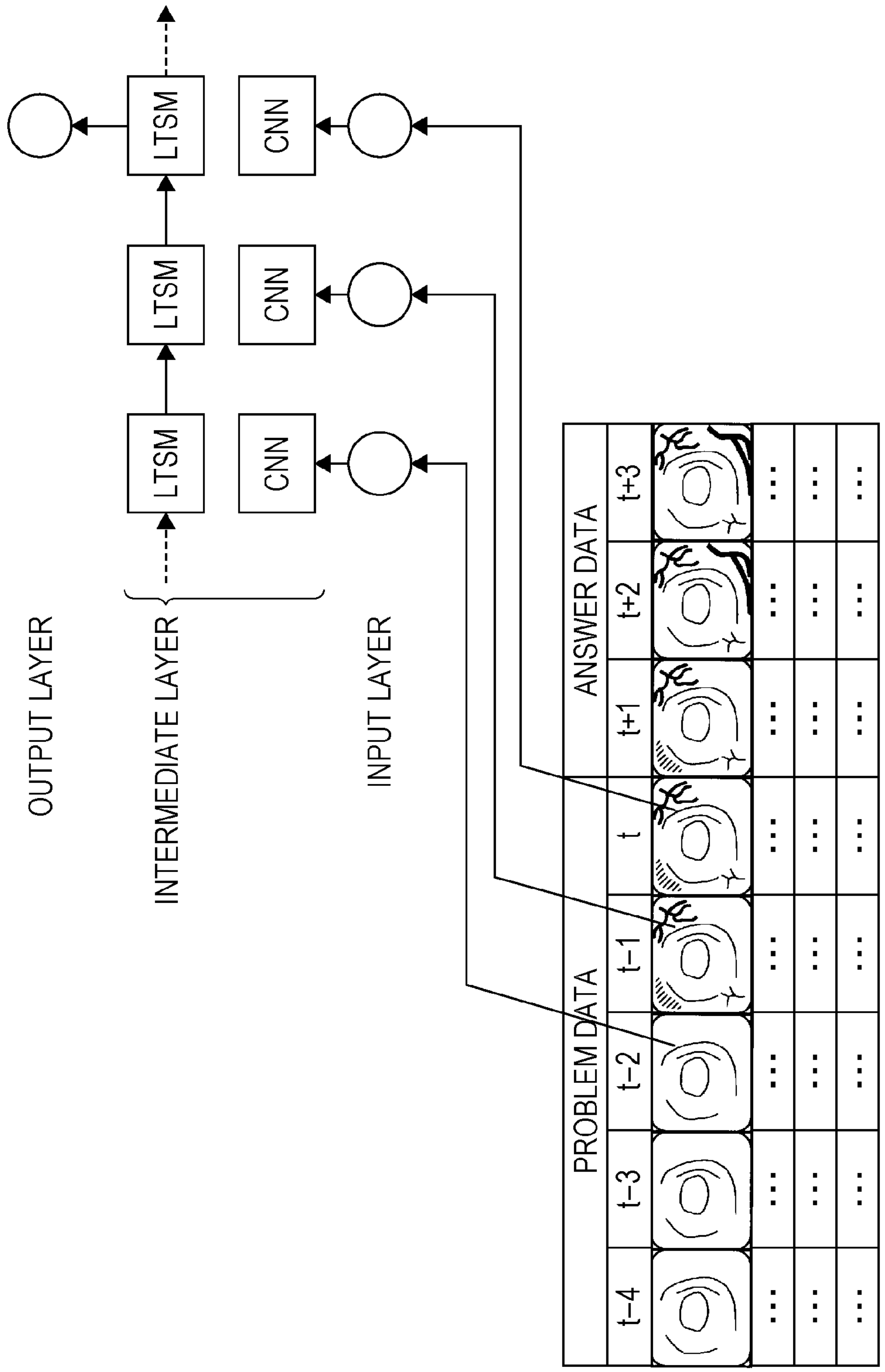
FIG. 19 is an explanatory diagram regarding processing of generating an endoscope-image-learned model according to a fourth embodiment.

FIG. 19 is an explanatory diagram regarding processing of generating an endoscope-image-learned model 95 according to a fourth embodiment. The information processing apparatus 6 constructs (generates) a neural network that receives a plurality of time-series endoscope images and outputs an endoscope image at the next time point by performing learning on the basis of training data having the plurality of time-series endoscope images as the problem data and having the endoscope image of the next time point of the last data in time series as the answer data.

The plurality of time-series endoscope images, which are the training data, are a plurality of time-series endoscope images of a predetermined intracorporeal part for each subject, and are generated on the basis of a plurality of endoscope images captured in each of past examinations performed multiple times. The endoscope image of the next time point, which is the answer data, is an endoscope image of the next time point (next time) of the last data in time series in the problem data, and corresponds to, for example, data (t+1) in FIG. 19. The answer data is not limited to a single data, and may include a plurality of data, that is, a plurality of endoscope images of the next time point (t+1) and the one after the next time point (t+2).

The input layer has one or more neurons that receive the plurality of time-series endoscope images, and transfers each of the plurality of input endoscope images to the intermediate layer. The intermediate layer has a multilayer structure in which a CNN and an RNN provided with the autoregressive layer after the convolution layer and the pooling layer are connected. The feature amount of each of the endoscope images input in time series is extracted by the convolution layer and the pooling layer. The autoregressive layer outputs the amount of change in each of the extracted feature amounts. The output layer has one or more neurons, and generates and outputs the endoscope image of the next time point on the basis of the amount of change in the feature amount of each of the endoscope images output from the intermediate layer. The training for the neural network forming a connection structure with the CNN and the RNN is performed, for example, by combining backpropagation and backpropagation through time (BPTT).

Figure 20:
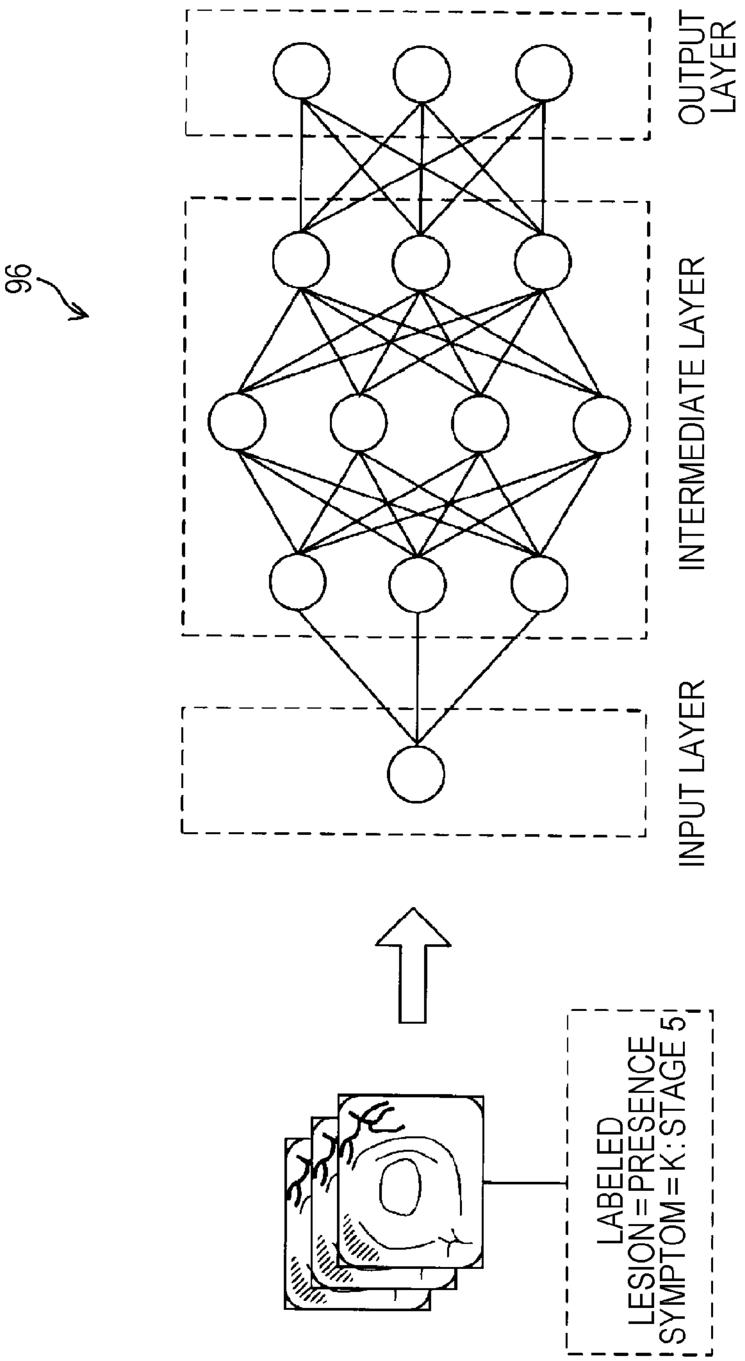
FIG. 20 is an explanatory diagram regarding processing of generating a lesion-learned model.

FIG. 20 is an explanatory diagram regarding processing of generating the lesion-learned model 96. The information processing apparatus 6 constructs (generates) a neural network that receives the endoscope image and outputs the presence or absence of a lesion and the stage of a symptom by performing learning on the basis of training data having the endoscope image as the problem data and having the presence or absence of a lesion and the stage of a symptom as the answer data. The endoscope image includes, for example, an intracorporeal part suspected of being a lesion. The presence or absence of a lesion and the stage of a symptom are information regarding the lesion and the stage of the symptom related to the intracorporeal part included in the endoscope image.

The input layer has a plurality of neurons that receive the input of a pixel value of the endoscope image, and transmits the input pixel value and distance information to the intermediate layer. The intermediate layer has a plurality of neurons that extract the image feature amount of the endoscope image, and transfers the extracted image feature amount to the output layer. The output layer has one or more neurons that output information regarding the presence or absence of a lesion and the stage of a symptom, and outputs information regarding the presence or absence of a lesion and the stage of a symptom on the basis of the image feature amount output from the intermediate layer. The lesion-learned model 96 may be a CNN, similarly to the peristalsis-amount-learned model 91.

Figure 21:
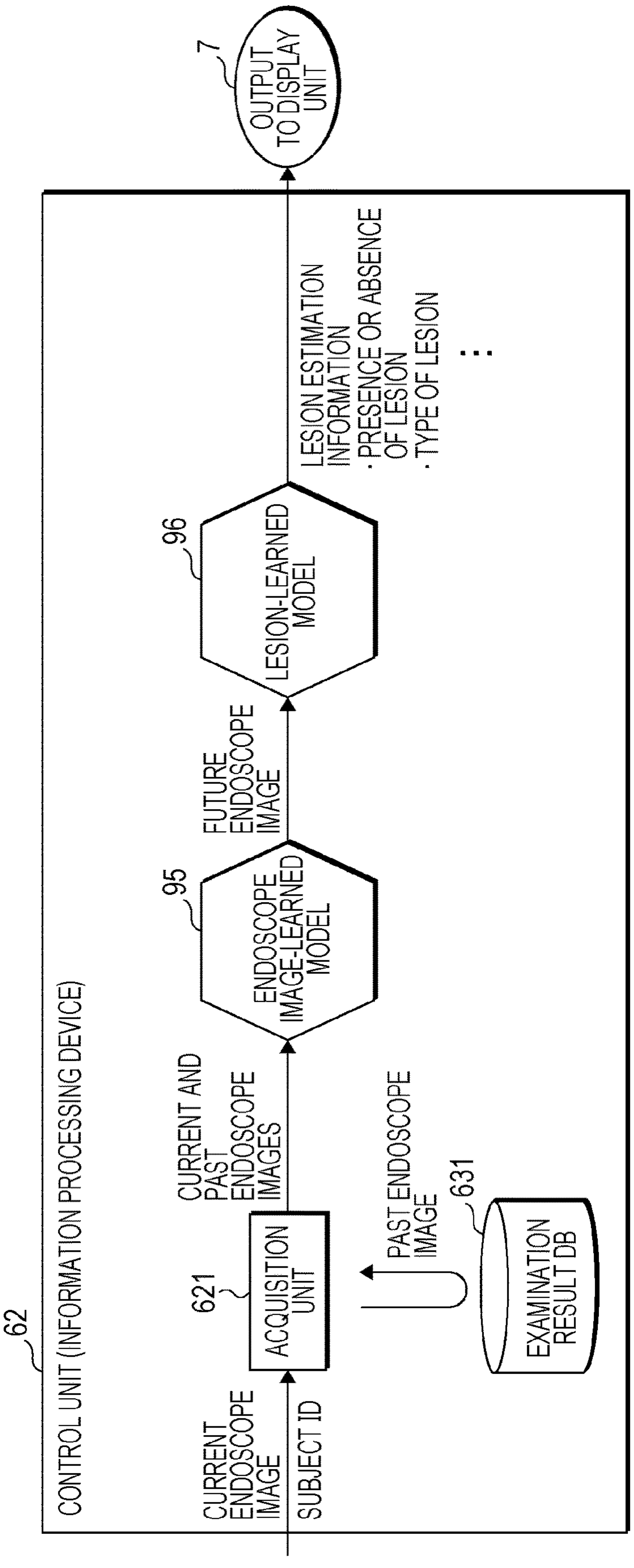

FIG. 21 is a functional block diagram illustrating functional parts included in the control unit 62 of the information processing apparatus 6 or the like. The control unit 62 executes the program P stored in the storage unit 63 to function as the acquisition unit 621. The control unit 62 executes the program P stored in the storage unit 63 or reads an entity file constituting a learned model such as the endoscope-image-learned model 95 to function as the endoscope-image-learned model 95 and the lesion-learned model 96.

The acquisition unit 621 acquires the endoscope image and the subject ID output by the processor 20 for an endoscope similarly to the first embodiment. The acquisition unit 621 acquires a plurality of endoscope images obtained in the past examinations performed on the subject by referring to the examination result DB 631 on the basis of the subject ID. The acquisition unit 621 extracts a feature amount from the surface shape, the color information, or the like on the basis of the endoscope images (the endoscope images of the current examination) output by the processor 20 for an endoscope, and specifies an endoscope image including an intracorporeal part (a part suspected of being a lesion) corresponding to the feature amount. The endoscope image to be specified (specific endoscope image) may be, for example, one frame (still image) of the endoscope image including the intracorporeal part or a moving image of several frames. The acquisition unit 621 specifies an endoscope image (past specific endoscope image) corresponding to the specific endoscope image among a plurality of past endoscope images (endoscope images obtained in a plurality of past examinations) on the basis of the specific endoscope image specified among the endoscope images of the current examination. The acquisition unit 621 generates object array data in which each of a plurality of specific time-series endoscope images from the past to the present is set as each element in an array on the basis of the current and past specific endoscope images. The acquisition unit 621 inputs the plurality of generated time-series specific endoscope images (object array data) to the endoscope-image-learned model 95.

The endoscope-image-learned model 95 inputs the plurality of specific time-series endoscope images output from the acquisition unit 621 to the input layer, generates a specific endoscope image of the next time point (the next time point of the last specific endoscope image in time series) output from the output layer, and outputs the generated specific endoscope image to the lesion-learned model 96. The specific endoscope image output from the endoscope-image-learned model 95 is estimated as a specific endoscope image including a future intracorporeal part (a part suspected of being a lesion).

The lesion-learned model 96 inputs the specific endoscope image output from the endoscope-image-learned model 95 to the input layer, and outputs lesion estimation information such as the presence or absence of a lesion and the stage of a symptom output from the output layer to the display unit 7.

Figure 22:
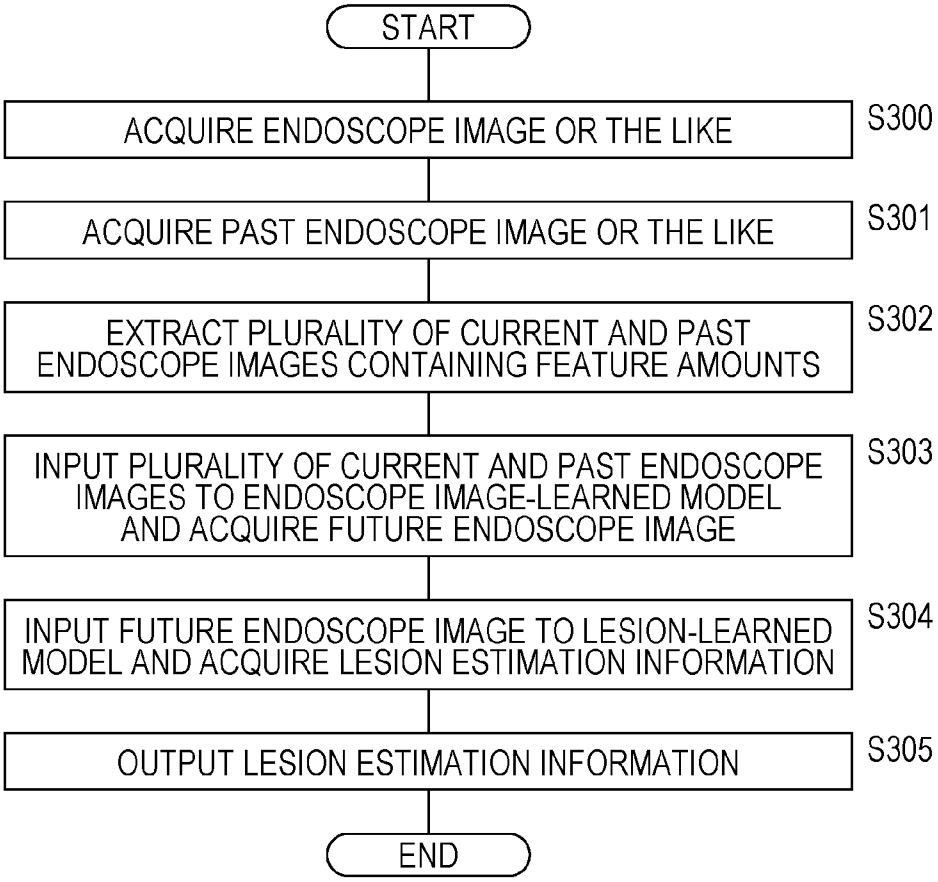
FIG. 22 is a flowchart illustrating an example of a processing procedure performed by the control unit of the information processing apparatus.

FIG. 22 is a flowchart illustrating an example of a processing procedure performed by the control unit 62 of the information processing apparatus 6. For example, the information processing apparatus 6 starts the processing of the flowchart on the basis of a content input through the input unit 8 connected to the information processing apparatus 6 itself.

The control unit 62 of the information processing apparatus 6 acquires the endoscope image or the like (S300). Similarly to the second embodiment, the control unit 62 acquires the endoscope image and the subject ID from the endoscope device 10.

The control unit 62 of the information processing apparatus 6 acquires the past endoscope image or the like (S301). The control unit 62 acquires the past endoscope image of the subject by referring to the examination result DB 631 on the basis of the subject ID.

The control unit 62 of the information processing apparatus 6 extracts a plurality of current and past endoscope images including the feature amount (S302). The control unit 62 extracts a feature amount from the surface shape, color information, or the like from the plurality of current and past endoscope images, and specifies an endoscope image (specific endoscope image) including an intracorporeal part (a part suspected of being a lesion) corresponding to the feature amount.

The control unit 62 of the information processing apparatus 6 inputs the plurality of current and past endoscope images to the endoscope-image-learned model 95, and acquires a future endoscope image (S303). The control unit 62 generates, for example, object array data including a plurality of time-series specific endoscope images by using the plurality of specified current and past endoscope images (specific endoscope images), and inputs the object array data to the endoscope-image-learned model 95. Then, the control unit 62 acquires a future endoscope image (specific endoscope image) output by the endoscope-image-learned model 95.

The control unit 62 of the information processing apparatus 6 inputs the future endoscope image to the lesion-learned model 96 and acquires the lesion estimation information (S304). The control unit 62 inputs the future endoscope image (specific endoscope image) to the lesion-learned model 96, and acquires the lesion estimation information such as the presence or absence of a lesion and the stage of a symptom output by the lesion-learned model 96.

The control unit 62 of the information processing apparatus 6 outputs the lesion estimation information (S305). The control unit 62 outputs the acquired lesion estimation information such as the presence or absence of a lesion and the stage of a symptom to the display unit 7 such as a display. Similarly to the second embodiment, the control unit 62 may derive the diagnosis support information such as an improvement proposal or the insurance support information such as an estimated insurance premium on the basis of the lesion estimation information, and output the derived information to the display unit 7.

According to the present embodiment, in a case where the past endoscope images captured in time series by the endoscope are input, the information processing apparatus 6 can efficiently generate the endoscope-image-learned model 95 that outputs a future endoscope image. Furthermore, the information processing apparatus 6 efficiently derives a future endoscope image by using the endoscope-image-learned model 95, and derives the lesion estimation information such as the presence or absence of a lesion on the basis of the derived future endoscope image. Therefore, it is possible to improve the estimation accuracy of the lesion estimation information.

The embodiments disclosed this time should be considered to be exemplary in all respects without being limited. The technical features described in the respective embodiments can be combined with each other, and the scope of the present invention is intended to include all modifications within the scope of the claims and the scope equivalent to the claims.

REFERENCE SIGNS LIST

S diagnosis support system
10 endoscope device
15 keyboard
16 storage shelf
20 processor for endoscope
21 control unit
211 image processing unit
212 distance information deriving unit
22 main storage device
23 auxiliary storage device
24 communication unit
25 touch panel
26 display device I/F
27 input device I/F
28 reading unit
31 endoscope connector
311 electric connector
312 optical connector
33 light source
34 pump
35 water supply tank
36 air/water supply port
40 endoscope
43 operation unit
431 control button
433 bending knob
44 insertion portion
441 soft portion
442 bending portion
443 distal tip
45 bend preventing portion
48 scope connector
49 flexible light guide tube
50 display device
6 information processing apparatus
61 communication unit
62 control unit
621 acquisition unit
622 peristalsis amount correction unit
623 feature amount deriving unit
624 difference information deriving unit
625 deterioration prediction line deriving unit
626 deterioration prediction value deriving unit
63 storage unit
631 examination result DB
632 recording medium
P program
64 input/output I/F
7 display unit
8 input unit
91 peristalsis-amount-learned model
92 deterioration-amount-learned model
93 corrected-deterioration-amount-learned model
94 difference-learned model
95 endoscope-image-learned model
96 lesion-learned model

The invention claimed is:

1. A non-transitory computer readable medium configured to store a program causing a computer to execute plural operations predicting the deterioration amount of a suspected lesion in an organ inner wall of a subject over time, comprising:

i) acquiring a plurality of images captured by an image sensor of an endoscope over a predetermined period;
ii) generating distance information on the distance from the image sensor to the organ inner wall and the suspected lesion from the images captured by the image sensor and data from a three-axis acceleration sensor, a gyro sensor, a geomagnetic sensor, or a magnetic coil sensor, using a monocular distance image estimation, a time of flight method, or a pattern irradiation method;
iii) generating a three-dimensional map of the organ inner wall and the suspected lesion therein generated based on the received captured images and the determined distance;
iv) estimating a future state of an intracorporeal part included in the plurality of images on the basis of the plurality of acquired images by determining a deterioration amount prediction line representing the deterioration amount of a suspected lesion in the organ inner wall as a function of time, wherein the intracorporeal part includes the organ inner wall;

v) acquiring the distance from the image sensor to the suspected lesion in the organ inner wall, and the three-dimensional map of the organ inner wall from a first processor of the endoscope;

vi) correlating endoscope images and distances from image sensors of endoscopes to suspected lesions with first corrections correcting three-dimensional maps of organ inner walls to compensate for subject peristalsis;

vii) correcting the vertical arrangement of an organ surface in the three-dimensional map using one of the first corrections selected by optimizing a coefficient used in arithmetic processing of the correlation using back-propagation, thereby improving the accuracy of a deterioration prediction line derived from the three-dimensional map;

viii) determining a shape, color, or position of the suspected lesion from the corrected three-dimensional map;

ix) superimposing the corrected three-dimensional map on a stored and previously-obtained three-dimensional map of the organ inner wall of the same subject;

x) determining a first difference between values of the shape of the corrected three-dimensional map and values of the shape of the previously-obtained three-dimensional map stored in a database;

xi) determining a second difference between values of the saturation, hue, and luminosity in a color space of the surface of the organ inner wall of the corrected three-dimensional map and values of the saturation, hue, and luminosity in the color space of the surface of the organ inner wall of the previously-obtained three-dimensional map;

xii) correlating the first and second difference data of subjects and a biological attribute of the subjects with deterioration amounts of suspected lesions of the subjects;

xiii) searching the database for a past deterioration amount of the suspected lesion of the subject;

xiv) determining the deterioration amount prediction line from the current and past deterioration amounts using a linear approximation, a logarithmic approximation, a polynomial approximation, a power approximation, or an exponential approximation;

xv) correcting the deterioration amount prediction line with a correction coefficient stored in a correction coefficient table storing plural correction coefficients, the physical attribute of the subject, and physical condition information about the physical condition of the subject and stored in the database, thereby improving the accuracy of the deterioration amount prediction line;

xvi) determining a deterioration amount prediction value for the elapse of a predetermined period of time from the deterioration amount prediction line; and xvii) displaying diagnosis support information based on the deterioration amount prediction value when the deterioration amount prediction value is larger than a predetermined deterioration threshold value determined by the severity of the suspected lesion, and displaying a message that there is no medical opinion when the deterioration amount prediction value is smaller than the predetermined deterioration threshold.

2. An information processing method causing a computer to execute processing predicting the deterioration amount of a suspected lesion in an organ inner wall of a subject over time, comprising:

i) acquiring a plurality of images captured by an image sensor of an endoscope over a predetermined period;

ii) generating distance information on the distance from the image sensor to the organ inner wall and the suspected lesion from the images captured by the image sensor and data from a three-axis acceleration sensor, a gyro sensor, a geomagnetic sensor, or a magnetic coil sensor, using a monocular distance image estimation, a time of flight method, or a pattern irradiation method;

iii) generating a three-dimensional map of the organ inner wall and the suspected lesion therein generated based on the received captured images and the determined distance;

iv) estimating a future state of an intracorporeal part included in the plurality of images on the basis of the plurality of acquired images by determining a deterioration amount prediction line representing the deterioration amount of a suspected lesion in the organ inner wall as a function of time, wherein the intracorporeal part includes the organ inner wall;

v) acquiring the distance from the image sensor to the suspected lesion in the organ inner wall, and the three-dimensional map of the organ inner wall from a first processor of the endoscope;

vi) correlating endoscope images and distances from image sensors of endoscopes to suspected lesions with first corrections correcting three-dimensional maps of organ inner walls to compensate for subject peristalsis;

vii) correcting the vertical arrangement of an organ surface in the three-dimensional map using one of the first corrections selected by optimizing a coefficient used in arithmetic processing of the correlation using back-propagation, thereby improving the accuracy of a deterioration prediction line derived from the three-dimensional map;

viii) determining a shape, color, or position of the suspected lesion from the corrected three-dimensional map;

ix) superimposing the corrected three-dimensional map on a stored and previously-obtained three-dimensional map of the organ inner wall of the same subject;

x) determining a first difference between values of the shape of the corrected three-dimensional map and values of the shape of the previously-obtained three-dimensional map stored in a database;

xi) determining a second difference between values of the saturation, hue, and luminosity in a color space of the surface of the organ inner wall of the corrected three-dimensional map and values of the saturation, hue, and luminosity in the color space of the surface of the organ inner wall of the previously-obtained three-dimensional map;

xii) correlating the first and second difference data of subjects and a biological attribute of the subjects with deterioration amounts of suspected lesions of the subjects;

xiii) searching the database for a past deterioration amount of the suspected lesion of the subject;

xiv) determining the deterioration amount prediction line from the current and past deterioration amounts using a linear approximation, a logarithmic approximation, a polynomial approximation, a power approximation, or an exponential approximation;

xv) correcting the deterioration amount prediction line with a correction coefficient stored in a correction coefficient table storing plural correction coefficients, the physical attribute of the subject, and physical condition information about the physical condition of the subject and stored in the database, thereby improving the accuracy of the deterioration amount prediction line;

xvi) determining a deterioration amount prediction value for the elapse of a predetermined period of time from the deterioration amount prediction line; and xvii) displaying diagnosis support information based on the deterioration amount prediction value when the deterioration amount prediction value is larger than a predetermined deterioration threshold value determined by the severity of the suspected lesion, and displaying a message that there is no medical opinion when the deterioration amount prediction value is smaller than the predetermined deterioration threshold.

3. The information processing method according to claim 2, wherein information regarding an insurance premium of a subject to be estimated is derived on the basis of the deterioration prediction value.

4. An information processing apparatus predicting the deterioration amount of a suspected lesion in an organ inner wall of a subject over time, comprising:

a first processor configured to i) acquire a plurality of images captured by an image sensor of an endoscope over a predetermined period, ii) generate distance information on the distance from the image sensor to the organ inner wall and the suspected lesion therein from the images captured by the image sensor and data from data from a three-axis acceleration sensor, a gyro sensor, a geomagnetic sensor, or a magnetic coil sensor, using a monocular distance image estimation, a time of flight method, or a pattern irradiation method, and iii) generate a three-dimensional map of the organ inner wall and the suspected lesion therein generated based on the received captured images and the determined distance; and a second processor in communication with the first processor and configured to iv) estimate a future state of an intracorporeal part included in the plurality of images on the basis of the plurality of acquired images by determining a deterioration amount prediction line representing the deterioration amount of a suspected lesion in the organ inner wall as a function of time, wherein the intracorporeal part includes the organ inner wall, v) acquiring the distance from the image sensor to the suspected lesion in the organ inner wall, and a three-dimensional map of the organ inner wall from a first processor of the endoscope, vi) correlating endoscope images and distances from image sensors of endoscopes to suspected lesions with first corrections correcting three-dimensional maps of organ inner walls to compensate for subject peristalsis, vii) correcting the vertical arrangement of an organ surface in the three-dimensional map using one of the first corrections selected by optimizing a coefficient used in arithmetic processing of the correlation using backpropagation, viii) determining a shape, color, or position of the suspected lesion from the corrected three-dimensional map, ix) superimposing the corrected three-dimensional map on a stored and previously-obtained three-dimensional map of the organ inner wall of the same subject, x) determining a first difference between values of the shape of the corrected three-dimensional map and values of the shape of the previously-obtained three-dimensional map stored in a database, xi) determining a second difference between values of the saturation, hue, and luminosity in a color space of the surface of the organ inner wall of the corrected three-dimensional map and values of the saturation, hue, and luminosity in the color space of the surface of the organ inner wall of the previously-obtained three dimensional map, xii) correlating the first and second difference data of subjects and a biological attribute of the subjects with deterioration amounts of suspected lesions of the subjects, xiii) searching the database for a past deterioration amount of the suspected lesion of the subject, xiv) determining the deterioration amount prediction line from the current and past deterioration amounts using a linear approximation, a logarithmic approximation, a polynomial approximation, a power approximation, or an exponential approximation, xv) correcting the deterioration amount prediction line with a correction coefficient stored in a correction coefficient table storing plural correction coefficients, the physical attribute of the subject, and physical condition information about the physical condition of the subject and stored in the database, thereby improving the accuracy of the deterioration amount prediction line, xvi) determining a deterioration amount prediction value for the elapse of a predetermined period of time from the deterioration amount prediction line, and xvii) displaying diagnosis support information based on the deterioration amount prediction value when the deterioration amount prediction value is larger than a predetermined deterioration threshold value determined by the severity of the suspected lesion, and displaying a message that there is no medical opinion when the deterioration amount prediction value is smaller than the predetermined deterioration threshold.

* * * * *